US011529194B2

(12) United States Patent
De Wijs et al.

(10) Patent No.: US 11,529,194 B2
(45) Date of Patent: Dec. 20, 2022

(54) WIRELESS POSITION DETERMINATION

(71) Applicant: KONINKLIJKE PHILIPS N.V., Eindhoven (NL)

(72) Inventors: Willem-Jan Arend De Wijs, Oss (NL); Gerardus Johannes Nicolaas Doodeman, Veldhoven (NL); Jacobus Josephus Leijssen, Waalre (NL); Michiel De Jong, Nuenen (NL); Jan Harm de Boer, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 620 days.

(21) Appl. No.: 16/086,342

(22) PCT Filed: Mar. 20, 2017

(86) PCT No.: PCT/EP2017/056486
§ 371 (c)(1),
(2) Date: Sep. 19, 2018

(87) PCT Pub. No.: WO2017/167594
PCT Pub. Date: Oct. 5, 2017

(65) Prior Publication Data
US 2019/0090957 A1    Mar. 28, 2019

(30) Foreign Application Priority Data
Mar. 31, 2016 (EP) .................................... 16163155

(51) Int. Cl.
*A61B 34/20* (2016.01)
*A61B 8/08* (2006.01)
(Continued)

(52) U.S. Cl.
CPC ............ *A61B 34/20* (2016.02); *A61B 8/0841* (2013.01); *A61B 8/4254* (2013.01);
(Continued)

(58) Field of Classification Search
CPC ....... A61B 34/20; A61B 8/4254; A61B 90/39; A61B 8/5261; A61B 17/3043;
(Continued)

(56) References Cited

U.S. PATENT DOCUMENTS 3,713,133 A    1/1973 Nathans
6,198,963 B1    3/2001 Haim et al.
(Continued)

FOREIGN PATENT DOCUMENTS

WO    2005033719 A1    4/2005

OTHER PUBLICATIONS

Lucas, Valentina S et al. "Utility of high-frequency ultrasound: moving beyond the surface to detect changes in skin integrity." Plastic surgical nursing : official journal of the American Society of Plastic and Reconstructive Surgical Nurses vol. 34,1 (2014) (Year: 2014).*
(Continued)

*Primary Examiner* — Luther Behringer
*Assistant Examiner* — Adil Partap S Virk

(57) ABSTRACT

The present invention relates to a system SY for determining a position of an RF transponder circuit RTC respective an ultrasound emitter unit UEU. The RF transponder circuit RTC emits RF signals that are modulated based on received ultrasound signals that are emitted or reflected by the ultrasound emitter unit UEU. The position of the RF transponder circuit RTC respective the ultrasound emitter unit UEU is determined based on a time difference ΔT1 between the emission of an ultrasound signal by the ultrasound emitter unit UEU and the detection by the RF detector unit RFD of a corresponding modulation in the RF signal emitted or reflected by the RF transponder circuit (RTC).

23 Claims, 6 Drawing Sheets

(51) Int. Cl.
*G06K 7/10* (2006.01)
*A61B 8/00* (2006.01)
*G01S 13/88* (2006.01)
*G01S 13/75* (2006.01)
*G01S 13/86* (2006.01)
*G01S 13/76* (2006.01)
*A61B 90/00* (2016.01)
*A61B 17/34* (2006.01)
*A61M 25/01* (2006.01)

(52) U.S. Cl.
CPC ........ *A61B 8/5261* (2013.01); *A61B 17/3403* (2013.01); *A61B 90/39* (2016.02); *G01S 13/758* (2013.01); *G01S 13/765* (2013.01); *G01S 13/862* (2013.01); *G01S 13/887* (2013.01); *G06K 7/10118* (2013.01); *A61B 2017/3413* (2013.01); *A61B 2034/2051* (2016.02); *A61B 2034/2063* (2016.02); *A61B 2034/2065* (2016.02); *A61B 2090/3762* (2016.02); *A61B 2090/392* (2016.02); *A61B 2090/3925* (2016.02); *A61B 2090/3937* (2016.02); *A61B 2090/3954* (2016.02); *A61B 2090/3958* (2016.02); *A61B 2090/3966* (2016.02); *A61B 2090/3975* (2016.02); *A61M 25/0108* (2013.01)

(58) Field of Classification Search
CPC .......... A61B 8/0841; A61B 2090/3925; A61B 2090/3966; A61B 2090/3937; A61B 2090/392; A61B 2034/2051; A61B 2090/3954; A61B 2034/2065; A61B 2090/3762; A61B 2090/3958; A61B 2090/3975; A61B 2034/2063; A61B 2017/3413; G06K 7/10118; G01S 13/887; G01S 13/758; G01S 13/862; G01S 13/765; A61M 25/0108
See application file for complete search history.

(56) References Cited

U.S. PATENT DOCUMENTS

| | | | |
|---|---|---|---|
| 7,549,960 | B2 | 6/2009 | Govari |
| 7,575,550 | B1* | 8/2009 | Govari ............ A61B 5/06 600/424 |
| 2002/0011932 | A1* | 1/2002 | Rodgers ............ G06K 19/0723 340/572.1 |
| 2002/0065455 | A1* | 5/2002 | Ben-Haim ........ A61B 5/0215 600/407 |
| 2002/0107445 | A1* | 8/2002 | Govari ............ A61B 90/39 600/437 |
| 2007/0090926 | A1 | 4/2007 | Potyrail et al. |
| 2009/0281419 | A1* | 11/2009 | Troesken ............ A61B 90/98 600/424 |
| 2010/0167644 | A1 | 7/2010 | Winter et al. |
| 2011/0004059 | A1* | 1/2011 | Arneson ............ A61B 1/00041 600/109 |
| 2011/0043429 | A1 | 2/2011 | Merlin |
| 2011/0319756 | A1* | 12/2011 | Zheng ............ G01S 7/52022 600/438 |
| 2012/0235847 | A1 | 9/2012 | Viikari et al. |
| 2012/0289827 | A1* | 11/2012 | Ismail ............ A61B 5/0035 600/430 |
| 2014/0024945 | A1 | 1/2014 | Mung et al. |

OTHER PUBLICATIONS

RFID handbook—Fundamentals and Applications in contactless smart cards, radio frequency identification and near field communication, Third Edition, Klaus Finkenzeller, Giesecke & Devrient GmbH, Germany, Wiley, 2010, ISBN: 978-0-470-69506-7.

The RF and Microwave handbook, 2001, Editor in Chief Mike Golio, CRC press, ISBN 13:978-1-4200-3676-3.

* cited by examiner

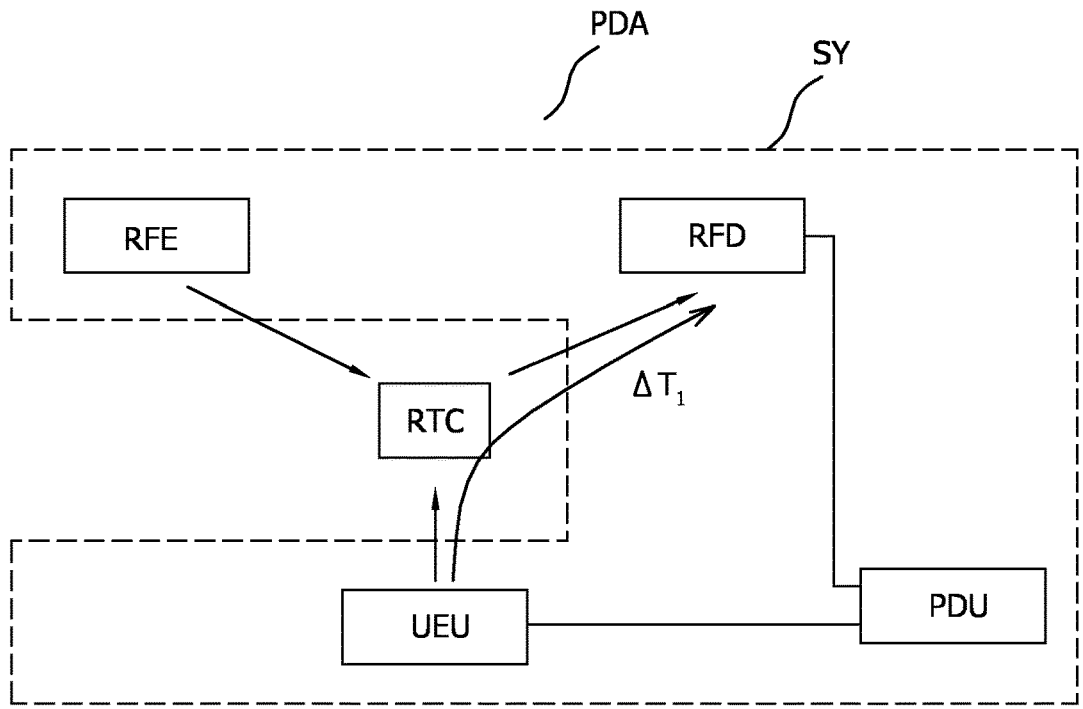
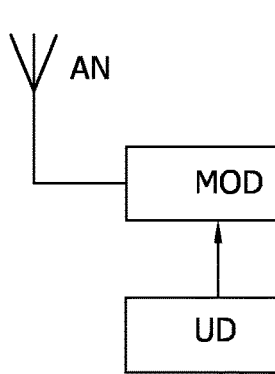
FIG. 2
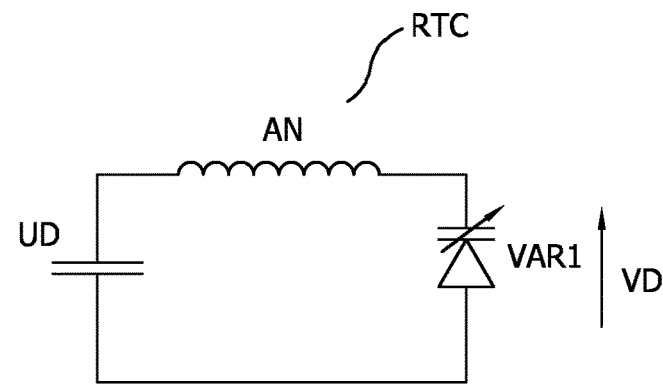
FIG. 3
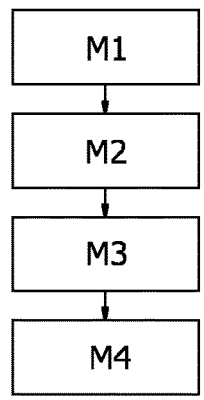
FIG. 4

WIRELESS POSITION DETERMINATION

CROSS-REFERENCE TO PRIOR APPLICATIONS

This application is the U.S. National Phase application under 35 U.S.C. § 371 of International Application Serial No. PCT/EP2017/056486, filed on Mar. 20, 2017, which claims the benefit of European Patent Application No. 16163155.1, filed on Mar. 31, 2016. This application is hereby incorporated by reference herein.

FIELD OF THE INVENTION

The invention relates to wireless position determination. An RF transponder circuit is disclosed that may be attached to objects in general for tracking their position. The RF transponder circuit may be used in a wide range of industries including consumer products and healthcare devices. In one particular application, the RF transponder circuit may be attached to a medical device such as catheter or a needle in order to track its position in the ultrasound field of an ultrasound imaging probe. A system for tracking the RF transponder circuit is also disclosed.

BACKGROUND OF THE INVENTION

In many areas of industry it is advantageous to be able to track an object's position. Further advantages arise from the ability to do this wirelessly. In the medical field in particular it is beneficial to wirelessly track the position of interventional devices such as catheters and needles in order to determine their position within a region of interest during a medical procedure. The position of the interventional device may subsequently be mapped to a corresponding medical image of the region of interest such as an ultrasound, computed tomography i.e. CT, positron emission tomography i.e. PET, single photon emission computed tomography i.e. SPECT image. Such a mapping can improve the visibility of the tracked device as well as improve identification of its position in relation to features in the medical image.

A document U.S. Pat. No. 7,575,550B1 describes an apparatus for determining the disposition of an object relative to a reference frame. The apparatus includes a field generator which generates an electromagnetic field in a vicinity of the object and a transducer which is fixed to the object. The transducer vibrates at a predetermined vibrational frequency in accordance with principles disclosed in document U.S. Pat. No. 3,713,133A and emits energy, responsive to an interaction of the electromagnetic field therewith. A detector in a vicinity of the object is utilized to detect the energy emitted by the transducer and generate signals in response thereto. A signal processor is also included for receiving and processing the detector signals to determine coordinates of the object.

Drawbacks of known tracking systems include the need to use high power generators and transducers in order to perform accurate tracking, especially when the separation between the tracking system and the tracked object is large. Moreover, existing systems can be somewhat difficult to miniaturize.

SUMMARY OF THE INVENTION

Thereto, a system SY for determining a position of an RF transponder circuit RTC respective an ultrasound emitter unit UEU based on RF signals emitted or reflected by the RF transponder circuit RTC is provided. The system includes an RF emitter unit RFE, an RF detector unit RFD, an ultrasound emitter unit UEU and a position determination unit PDU. The RF emitter unit RFE is configured to emit RF signals for energizing the RF transponder circuit RTC. The RF detector unit RFD is configured to detect RF signals emitted or reflected by the RF transponder circuit RTC. The ultrasound emitter unit UEU is configured to emit ultrasound signals for modulating the RF signals emitted or reflected by the RF transponder circuit RTC. Moreover, the position determination unit PDU is in operative communication with the RF detector unit RFD and with the ultrasound emitter unit UEU, and is configured to determine a position of the RF transponder circuit RTC respective the ultrasound emitter unit UEU based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC.

In order to track the position of the RF transponder circuit RTC, RF signals emitted by the RF emitter unit RFE, energize, i.e. deliver power to, the RF transponder circuit RTC. Ultrasound signals emitted by the ultrasound emitter unit UEU modulate RF signals emitted or reflected by the RF transponder circuit. The RF detector unit RFD detects the RF signals emitted or reflected by the RF transponder circuit RTC. The time delay between the emission of the ultrasound signal that ultimately modulates the RF signals emitted or reflected by the RF transponder circuit, and the detection by the RF detector unit RFD of the corresponding modulation in the RF signal emitted or reflected by the RF transponder circuit RTC is herein defined as $\Delta T_1$. Time delay $\Delta T_1$ is equal to the sum of the time period for the ultrasound signal to travel from the ultrasound emitter unit UEU to the RF transponder circuit RTC and the time period for the modulated RF signal to travel from the RF transponder circuit RTC to the RF detector unit RFD. Owing to the vast difference between the propagation speed of RF, at $3\times10^8$ m/s, and that of ultrasound, at approximately 330 m/s in air, time delay $\Delta T_1$ is substantially equal to the time period for the ultrasound signal to travel from the ultrasound emitter unit UEU to the RF transponder circuit RTC. The same substantial equivalence holds when the RF transponder circuit RTC is immersed or embedded in other media including the human body whose water-based composition provides an ultrasound propagation speed of approximately 1500 m/s. Thus a position of the RF transponder circuit RTC respective the ultrasound emitter unit UEU, or more particularly the range or distance between the ultrasound emitter unit UEU and the RF transponder circuit RTC, can be determined based on this time difference $\Delta T_1$. This range can be calculated by multiplying time difference $\Delta T_1$ by the speed of ultrasound propagation in the medium between ultrasound emitter unit UEU and the RF transponder circuit RTC.

In another configuration, instead of being based on the above time difference $\Delta T_1$, or indeed in addition to being based on this time difference, the determined position of the RF transponder circuit RTC respective the ultrasound emitter unit UEU may include the angular position of the RF transponder circuit RTC respective the ultrasound emitter unit UEU. This angular position may for example be determined based on the direction of emission of the ultrasound signals by the ultrasound emitter unit UEU. This angular position may alternatively or additionally be based on the angular sensitivity of the ultrasound detector UD in the RF transponder circuit RTC. When used in combination with the time delay information, this angular position allows the position of the RF transponder circuit RTC to be determined respective the ultrasound emitter unit UEU in three dimensions.

In accordance with one aspect of the invention, ultrasound emitter unit UEU is configured to emit ultrasound signals at a frequency that is greater than or equal to 40 kHz. Ultrasound signals at frequencies below approximately 30 kHz are known to cause mechanical vibration in some structures. By using ultrasound frequencies that are greater than or equal to 40 kHz, interference with the position determination aspects of the system can be eliminated. The use of higher frequency ranges also means that shorter wavelength ultrasound signals are used. Such may provide even greater position determination accuracy.

In accordance with another aspect of the invention the RF emitter unit RFE of the system SY includes an RF emitter unit antenna for transmitting RF signals to the RF transponder circuit RTC. Moreover, the RF emitter unit antenna is coupled to the RF emitter unit RFE and to the RF detector unit RFD such that the RF emitter unit antenna also serves as an input to the RF detector unit RFD for detecting RF signals emitted or reflected by the RF transponder circuit RTC. By using the RF emitter unit antenna for both transmitting and receiving the RF signals the complexity of the electronic circuitry is reduced.

In accordance with another aspect of the invention the RF transponder circuit RTC has a mechanical resonance frequency. Moreover the ultrasound emitter unit UEU is configured to emit ultrasound signals at a frequency that is different to the mechanical resonance frequency of the RF transponder circuit RTC. In so doing, ultrasound-induced mechanical vibrations of the RF transponder circuit RTC are avoided, substantially eliminating the risk that such ultrasound-induced mechanical vibrations interfere with the modulation of the RF signal that is detected by the RF detector unit RFD.

In accordance with another aspect of the invention the modulation includes at least one of the following: i) changing a frequency of the RF signals emitted or reflected by the RF transponder circuit RTC; ii) changing a phase of the RF signals emitted or reflected by the RF transponder circuit RTC; iii) changing an amplitude of the RF signals emitted or reflected by the RF transponder circuit RTC; iv) changing a pulse sequence of the RF signals emitted or reflected by the RF transponder circuit RTC; v) changing a code encoded in the RF signals emitted or reflected by the RF transponder circuit RTC.

In accordance with another aspect of the invention the ultrasound emitter unit UEU2, UEU3 includes a plurality of ultrasound emitters $UE_{a1 \ldots an}$. Each of the emitters emits ultrasound signals in order to provide a set of time a set of time differences $\Delta T_{a1 \ldots an}$. The position determination unit PDU2, PDU3 determines a position of the RF transponder circuit RTC based on the set of time differences $\Delta T_{a1 \ldots an}$ between the emission of an ultrasound signal by each of the plurality of ultrasound emitters in the ultrasound emitter unit UEU2, UEU3 and the detection by the RF detector unit RFD of its corresponding modulation in the RF signal emitted or reflected by the RF transponder circuit RTC. Advantageously the accuracy of the determined position is improved.

In accordance with another aspect of the invention at least a second RF detector unit RFD2 is provided. Moreover, the position of the RF transponder circuit RTC respective the RF detector unit RFD and the at least a second RF detector unit RFD2 is determined based on a time delay $\Delta T_3$ between the time difference $\Delta T_1$ defined above and a time difference $\Delta T_2$ between the emission of the ultrasound signal by the ultrasound emitter unit UEU and the detection by the at least a second RF detector unit RFD2 of the corresponding modulation in the RF signal emitted or reflected by the RF transponder circuit RTC. Advantageously this improves the accuracy of the determined position.

In accordance with another aspect of the invention an RF transponder circuit RTC is disclosed. Advantageously the RF transponder circuit RTC electrically modulates RF signals emitted or reflected by the RF transponder circuit RTC, thereby improving the integrity of the position determination. Moreover the electrical modulation improves design freedom by allowing the miniaturization of the RTC.

In accordance with another aspect a wireless unit WU is disclosed. The wireless unit includes the RF transponder circuit RTC and i) a fiducial FID for being tracked by a magnetic tracking system or an optical or an ultrasound or an X-ray or a CT or a PET or a SPECT imaging system or ii) a transceiver unit TU responsive to at least one of ultrasound, electromagnetic, RF, microwave, infrared, and optical radiation. The fiducial FID or the transceiver unit TU is held in a fixed position with respect to the RF transponder circuit RTC; i.e. it is mechanically connected to the RF transponder circuit RTC.

In accordance with another aspect a tracking arrangement TA is disclosed. The tracking arrangement TA includes the wireless unit WU, the system SY, and a wireless unit tracking system WUTS comprising either i) a fiducial tracking system FTS or ii) a transceiver tracking unit TTU, configured to determine a position of the wireless unit WU based on signals transmitted between the i) fiducial tracking system FTS and the fiducial FID, or between the ii) transceiver tracking unit TTU and the transceiver unit TU, correspondingly. The fiducial tracking system FTS is either a magnetic tracking system or an optical or an ultrasound or an X-ray or a CT or a PET or a SPECT imaging system and is configured to provide an image that includes a position of the fiducial FID.

In accordance with another aspect a registration arrangement RA is disclosed. The registration arrangement RA includes the system SY; wherein the ultrasound emitter unit UEU of the system SY further includes i) a fiducial FID for being tracked by an optical imaging system or ii) a transceiver unit TU responsive to at least one of ultrasound, electromagnetic, RF, microwave, infrared, and optical radiation; and wherein the fiducial FID or the transceiver unit TU is held in a fixed position with respect to the ultrasound emitter unit UEU. The registration arrangement RA further includes an ultrasound emitter unit location determination unit ULDU comprising either i) a fiducial tracking system FTS or ii) a transceiver tracking unit TTU, configured to determine a position of the ultrasound emitter unit UEU based on signals transmitted between the i) fiducial tracking system FTS and the fiducial FID, or between the ii) transceiver tracking unit TTU and the transceiver unit TU, correspondingly. In this aspect the fiducial tracking system FTS is an optical imaging system and is configured to provide an image that includes a position of the fiducial FID.

Other aspects of the invention including method steps and a computer program product are defined in the independent claims.

BRIEF DESCRIPTION OF THE FIGURES

FIG. 1 illustrates a first embodiment of a position determination arrangement PDA that includes a system SY for determining a position of an RF transponder circuit RTC respective an ultrasound emitter unit UEU, together with an RF transponder circuit RTC.

FIG. 2 illustrates an RF transponder circuit RTC including an Antenna AN, an ultrasound detector UD and a modulator MOD.

FIG. 3 illustrates an RF transponder circuit RTC in which modulation is provided by a varactor diode VAR1 that forms part of a series LCR tuned circuit.

FIG. 4 illustrates various method steps of a position determination method that may be used with the system SY in FIG. 1.

DETAILED DESCRIPTION OF THE INVENTION

Figure 5A:
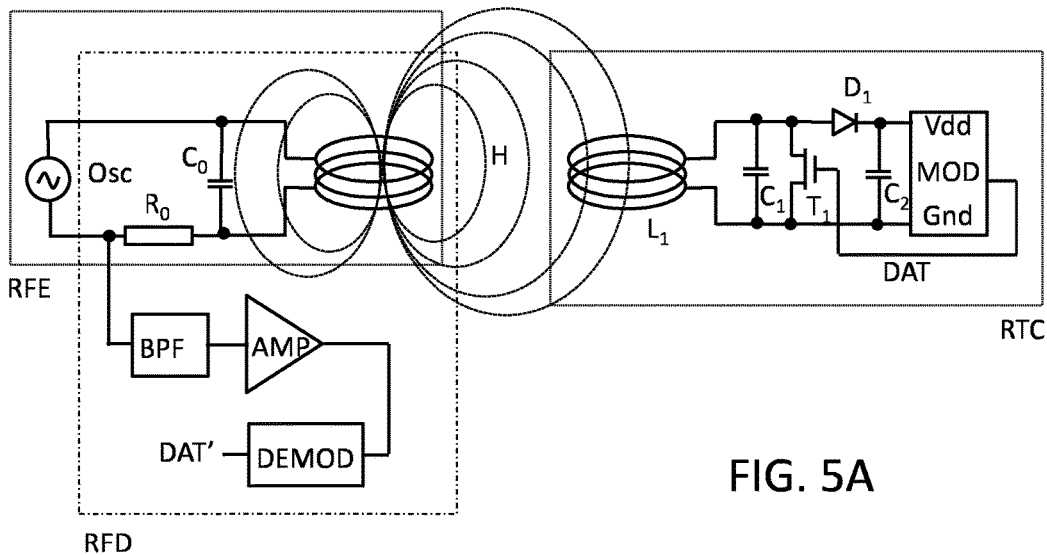
FIG. 5 illustrates, in FIG. 5A another exemplary RF transponder circuit RTC together with an exemplary RF emitter RFE and an exemplary RF detector RFD; and in FIG. 5B another exemplary RF transponder circuit RTC which employs load modulation to modulate backscattered radiation.

In order to illustrate the principles of the present invention, various embodiments are described in which an RF transponder circuit RTC is attached to a medical needle and a system SY is used to track the medical needle via the position of the RF transponder circuit RTC. In the medical application field it is also contemplated to attach the RF transponder circuit RTC to other medical or interventional devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device for use in their tracking. It is however to be appreciated that the RF transponder circuit RTC may be attached to objects in general for tracking their position. Moreover, whilst examples are provided in which the position of the RF transponder circuit RTC is tracked when it is immersed or embedded in air or water-based media, it is to be appreciated that tracking may be effected in the same manner when the RF transponder circuit RTC is immersed or embedded in media in general. The invention thus finds broader application in areas such as those in which Radiofrequency identification, i.e. RFID tags are currently used, in particular for object tracking, security, payment, and authentication purposes.

FIG. 1 illustrates a first embodiment of a position determination arrangement PDA that includes a system SY for determining a position of an RF transponder circuit RTC respective an ultrasound emitter unit UEU, together with an RF transponder circuit RTC. System SY includes RF emitter unit RFE, RF detector unit RFD, ultrasound emitter unit UEU and position determination unit PDU.

The RF emitter unit RFE in FIG. 1 is configured to emit RF signals for energizing RF transponder circuit RTC. RF signals are conventionally recognized as being within the frequency range from around 3 kHz to around 300 GHz. RF signals in this frequency range are suitable for the RF emitter unit RFE since these may be used to energize, i.e. transfer power to, the RF transponder circuit. As is described later, techniques such as those used in radio frequency identification, i.e. RFID technology, near field communication, i.e. NFC technology, and wireless power technology are contemplated for providing the desired power transfer to the RF transponder circuit RTC. The emitted RF signals may be pulsed or continuous wave; the latter being preferred in view of a simpler design.

RF emitter RFE in FIG. 1 may include an antenna (not shown in FIG. 1) for radiating the RF signals. Various types of antenna are suitable for this purpose including a stripline, slot, patch, coil, monopole or dipole antenna. It is also contemplated that RF emitter RFE may include an antenna array in which the phase of signals transmitted to each antenna in the array is set using known beamforming techniques on order to control the direction of RF emissions emitted by RF emitter unit RFE. The improved directivity offered by such beamforming techniques may advantageously reduce interference with nearby electronic systems or reduce the power of the RF emissions. Preferably the antenna is provided by an inductor in the form of a conductive coil. This may be arranged for transferring electrical power to a corresponding conductive coil in RF transponder circuit RTC. The antenna in RF transponder circuit RTC may thus operate in a similar way to the antenna in known RFID or NFC systems. Using the principles of RFID and NFC wireless power, energy transfer between RF emitter unit RFE and RF transponder circuit RTC may therefore be provided primarily by magnetic coupling between two inductive coils. It is also contemplated to transfer the power capacitively from the RF emitter unit to RF transponder circuit RTC, or through a combination of capacitive and inductive coupling in a manner similar to that used in RFID technology in which, for example in the far-field, power transfer typically takes place through a combination of these processes.

Optionally RF emitter RFE in FIG. 1 may share a common antenna with RF detector unit RFD in FIG. 1. Thereto, RF emitter unit RFE of system SY may include an RF emitter unit antenna for transmitting RF signals to the RF transponder circuit RTC. Moreover, the RF emitter unit antenna may be coupled to both the RF emitter unit RFE and the RF detector unit RFD such that the RF emitter unit antenna further serves as an input to the RF detector unit RFD for detecting RF signals emitted or reflected by the RF transponder circuit RTC. The coupling, or more specifically electrical coupling, may include hard-wiring both the RF emitter unit RFE and to the RF detector unit RFE, or may include a switch such as a mechanical or transistor switch for switching between the two units. By using the RF emitter unit antenna for both the detection and sensing or RF signals the complexity of the electronic circuitry is reduced.

Generally speaking the exact frequency of RF signals emitted by RF emitter RFE in FIG. 1 is not critical and other factors such as the availability of existing hardware and the size of RF antenna on the RF emitter unit RFE that transmits and on the RF transponder circuit RTC affect the actual frequency that is used. Thus RF frequencies, typically defined as those in the range 3 kHz to 300 GHz, are suitable for the frequency of RF signals emitted by RF emitter RFE. In order to provide efficient power transfer to the RF transponder circuit, preferably the RF transponder circuit RTC has a resonant frequency and preferably the RF signals emitted by the RF emitter unit RFE have a bandwidth that includes this resonant frequency. In water-based media the decrease in penetration depth with increasing frequency favors the use of lower frequencies within this range. For practical reasons a preferred frequency range of RF signals emitted by RF emitter unit RFE is from 1 MHz to 1000 MHz MHz, or from 2 MHz to 300 MHz, or from 10 MHz to 100 MHz. The specific frequencies of 252 MHz and 800 MHz advantageously limit interference from GSM communications and have reasonably high magnetic field penetration in water respectively.

Returning to FIG. 1, RF detector unit RFD in FIG. 1 is configured to detect RF signals emitted or reflected by RF transponder circuit RTC. Moreover, ultrasound emitter unit UEU is configured to emit ultrasound signals for modulating the RF signals emitted or reflected by the RF transponder circuit RTC. Thus, in operation the RF transponder circuit RTC receives RF signals that have been emitted by RF emitter unit RFE. RF transponder circuit RTC is energized, or powered by these received RF signals. RF transponder circuit RTC also receives ultrasound signals from ultrasound emitter unit UEU, and these ultrasound signals modulate the RF signals that are emitted or reflected by the RF transponder circuit RTC.

Whilst not illustrated, optionally, RF detector unit RFD and/or position determination unit PDU may additionally be in operative communication with RF emitter unit RFE and configured to receive a synchronization signal therefrom. Improved sensitivity and thus positioning accuracy of the RF transponder circuit RTC has been found to result from this. The synchronization signal may for example be the original, unmodulated RF signal emitted by RF emitter unit RFE. This may for example be received from RF emitter unit RFE by means of a wired link, and used to demodulate the RF signals emitted or reflected by RF transponder circuit RTC. Alternatively such a synchronization signal may be detected as part of the RF signal detected by RF detector unit RFD and recovered using known RF carrier-signal recovery techniques.

Ultrasound signals are conventionally recognized as being sound signals above approximately 20 kHz. This broad range of ultrasound signals is in general suitable for the ultrasound emissions of ultrasound emitter unit UEU. Owing to the increasing attenuation of ultrasound at high frequencies in water-based media it is favorable to use lower frequencies within this range in order to provide low power operation in such environments. Other factors including the provision of the ultrasound signals from existing hardware may also affect the choice of ultrasound frequency. Many, for example magnetostrictive, ultrasound transducers are readily available in the 20-40 kHz range and are suitable for this purpose. Piezoelectric transducers are also suitable, as are micro electro mechanical systems i.e. MEMS or capacitive micromachined ultrasound transducer i.e. CMUT—type transducers, the latter being well-suited to the generation of ultrasound signals in the MHz region. Moreover, the probe of an ultrasonic imaging system typically operates in the frequency range from 1 to 20 MHz, and, as described later in one embodiment, this may also serve as ultrasound emitter unit UEU. The various tradeoffs including the attenuation in water-based media and the availability of current hardware results in a preferred frequency range for the ultrasound emissions of the ultrasound emitter unit UEU of from 100 kHz-50 MHz, or from 1 MHz-20 MHz.

In order to avoid the risk that mechanical vibrations of the RF transponder circuit RTC that are induced by the received ultrasound signals, interfere with the intended, electrical modulation of the RF signal that is ultimately detected by the RF detector unit RFD, preferably the ultrasound emitter unit UEU in FIG. 1 is configured to emit ultrasound signals at a frequency that is different to the mechanical resonance frequency of the RF transponder circuit RTC. Moreover, when the RF transponder circuit RTC, as described later, is included in a wireless tag, it is likewise preferable that the ultrasound emitter unit UEU is configured to emit ultrasound signals at a frequency that is different to the mechanical resonance frequency of the wireless tag. By the term different it is meant that that the modulus of the difference between these frequencies expressed as a ratio of the mechanical resonance frequency preferably exceeds 10%, or 20% or 50% or 100%. A known position tracking system disclosed in document U.S. Pat. No. 3,713,133A cited above discloses a mechanically resonant tag with a resonance frequency of 20 kHz or 30 kHz. In the present invention it may thus be beneficial to use ultrasound frequencies that are in excess of 30 kHz in order to prevent the risk of such mechanical vibrations interfering with the desired electrical modulation by the RF transponder circuit RTC. Thus, in the present invention it may be beneficial that the ultrasound emitter unit UEU in FIG. 1 is configured to emit ultrasound frequencies that are greater than or equal to 40 kHz, i.e. >40 kHz, or >50 kHz, or >75 kHz, or >100 kHz, or >200 kHz, or >500 kHz, or >1 MHz, or >2 MHz, or >5 MHz, or >10 MHz. The corresponding RF transponder circuit RTC that is used in conjunction with the ultrasound emitter unit may optionally include an electrical filter that is configured to attenuate ultrasound signals that are less than the above disclosed ranges, i.e. less than 40 kHz and so on. This can be used to prevent inadvertent activation of the RF transponder circuit by stray ultrasound signals.

In more detail, in one example implementation the RF transponder circuit RTC in FIG. 1 may be provided by the RF transponder circuit RTC of FIG. 2. FIG. 2 illustrates an RF transponder circuit RTC including antenna AN, ultrasound detector UD and modulator MOD. Antenna AN in FIG. 2 converts RF signals that were emitted by RF emitter unit RFE in FIG. 1, into first electrical signals for energizing RF transponder circuit RTC in FIG. 2. Antenna AN may be provided by one of the antenna options described above in relation to the antenna of RF emitter unit RFE. Thus, antenna AN serves to provide wireless power to RF transponder circuit RTC. In a preferred embodiment Antenna AN is provided by an inductor in the form of a conductive coil that is arranged to receive electrical power from a corresponding inductor in the RF emitter unit RFE.

Ultrasound detector UD in FIG. 2 is configured to convert received ultrasound signals into second electrical signals. Thus, in operation, ultrasound detector UD receives ultrasound signals from ultrasound emitter unit UEU in FIG. 1 and converts these signals into second electrical signals. Various types of ultrasound detectors are suitable for use as ultrasound detector UD in FIG. 2 including piezoelectric, piezoresistive and capacitive detectors. More specifically, MEMS or CMUT-type ultrasound detectors may also be used. Suitable piezoelectric materials include polymer piezoelectric materials such as Polyvinylidene fluoride, a PVDF co-polymer such as polyvinylidene fluoride trifluoroethylene, or a PVDF ter-polymer such as P(VDF-TrFE-CTFE). Polymer piezoelectric materials offer high flexibility and thus may be conformally attached to surfaces having non-flat topography.

Modulator MOD in FIG. 2 is configured to receive the second electrical signals that were generated by ultrasound detector UD and to cause antenna AN to emit or reflect RF signals that are modulated based on the second electrical signals. In other words, RF transponder circuit RTC is arranged to emit or reflect RF signals that are electrically modulated based on received ultrasound signals.

Returning to FIG. 1, position determination unit PDU is in operative communication with the RF detector unit RFD and with ultrasound emitter unit UEU. Moreover, position determination unit PDU is configured to determine a position of the RF transponder circuit RTC respective the ultrasound emitter unit UEU based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC. In a preferred configuration position determination unit PDU periodically triggers ultrasound emitter unit UEU to generate an ultrasound signal, and subsequently monitor the time between the trigger signal and the detection by the RF detector unit RFD of a corresponding modulation in the RF signal emitted or reflected by the RF transponder circuit RTC. In another configuration ultrasound emitter unit UEU periodically issues ultrasound signals and provides a reference timing signal to position determination unit PDU from which the time difference $\Delta T_1$ is determined. Other configurations are clearly also possible. Position determination unit PDU may for example be provided by electronic circuitry or a processor.

FIG. 4 illustrates various method steps of a position determination method that may be used with the system SY in FIG. 1. Whilst illustrated in a linear manner, some of the method steps may be executed simultaneously. With reference to FIG. 4, the method may include the steps of:

M1: causing the RF emitter unit RFE to emit RF signals for energizing the RF transponder circuit RTC M2: causing the RF detector unit RFD to detect RF signals emitted or reflected by the RF transponder circuit RTC M3: causing the ultrasound emitter unit UEU to emit ultrasound signals for modulating the RF signals emitted or reflected by the RF transponder circuit RTC; and M4: determining a position of the RF transponder circuit RTC respective the ultrasound emitter unit UEU based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC.

The method may additionally include the effect of the above method step of: causing the ultrasound emitter unit UEU to emit ultrasound signals for modulating the RF signals emitted or reflected by the RF transponder circuit RTC;

which is to cause the RF signals emitted or reflected by the RF transponder circuit RTC to be modulated in response to the emitted ultrasound signals.

Moreover the above method steps, and/or other method steps disclosed herein, may be recorded in the form of instructions which when executed on a processor cause the processor to carry out these method steps. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

As illustrated in FIG. 1, the time delay between the emission of an ultrasound signal that ultimately modulates the RF signals emitted or reflected by RF transponder circuit RTC, and the detection by the RF detector unit RFD of the corresponding modulation in the RF signal emitted or reflected by the RF transponder circuit RTC is herein defined as $\Delta T_1$. Time delay $\Delta T_1$ is equal to the sum of the time period for the ultrasound signal to travel from the ultrasound emitter unit UEU to the RF transponder circuit RTC and the time period for the modulated RF signal to travel from the RF transponder circuit RTC to the RF detector unit RFD. Owing to the vast difference between the propagation speed of RF, at $3 \times 10^8$ m/s, and that of ultrasound, at approximately 330 m/s in air, time delay $\Delta T_1$ is substantially equal to the time period for the ultrasound signal to travel from the ultrasound emitter unit UEU to the RF transponder circuit RTC. Thus a position of the RF transponder circuit RTC respective the ultrasound emitter unit UEU, or more specifically the range or distance between the ultrasound emitter unit UEU and the RF transponder circuit RTC, can be determined based on this time difference $\Delta T_1$. This can be calculated by multiplying time difference $\Delta T_1$ by the speed of ultrasound propagation in the medium between ultrasound emitter unit UEU and the RF transponder circuit RTC. Similarly, the large differences in propagation speeds of RF and ultrasound in other media, including the human body which is largely water-based, allow a position of the RF transponder circuit RTC respective the ultrasound emitter unit UEU to be determined in the same manner when the RF transponder circuit RTC is immersed in media in general.

For example, in one contemplated arrangement the distance between the ultrasound emitter unit UEU and the RF transponder circuit RTC is 0.15 m and the medium therebetween is water having a speed of ultrasound propagation of 1480 m/s at 3 MHz. The exemplary distance between the RF transponder circuit RTC and the RF detector RFD is 0.25 m. Time difference $\Delta T_1$ is thus 101 microseconds+0.8 nanoseconds, and can be approximated to the first term alone, i.e. 101 microseconds, with negligible positioning error.

In another configuration, instead of being based on the above time difference $\Delta T_1$, or indeed in addition to being based on this time difference, the position of the RF transponder circuit RTC respective the ultrasound emitter unit UEU may include the angular position of the RF transponder circuit RTC respective the ultrasound emitter unit UEU. This angular position may for example be determined based on the direction of emission of ultrasound signals by the ultrasound emitter unit UEU. In one example implementation it is contemplated to provide ultrasound emitter unit UEU with an array ultrasound emitters. Such may be provided by the ultrasound emitter array of a beamforming ultrasound imaging system of the type described herein. Using beamforming techniques, the plurality of ultrasound emitters may be configured to generate a plurality of beams each having a predetermined emission angle respective the ultrasound emitter unit UEU. The angular position of RF transponder circuit RTC respective ultrasound emitter unit UEU may subsequently be determined by identifying the particular beam that was activated when the RF transponder circuit RTC caused a modulation in the RF signal that was emitted or reflected by the RF transponder circuit RTC.

In another configuration that is described later with reference to FIG. 9 and FIG. 10, ultrasound emitter unit UEU includes a plurality of ultrasound emitters and the position of RF transponder circuit RTC respective ultrasound emitter unit UEU is determined based on a set of time differences $\Delta T_{a1 \ldots an}$ between the emission of an ultrasound signal by each of the plurality of ultrasound emitters in the ultrasound emitter unit UEU and the detection by the RF detector unit RFD of its corresponding modulation in the RF signal emitted or reflected by the RF transponder circuit RTC.

The angular position of the RF transponder circuit RTC respective the ultrasound emitter unit UEU may alternatively or additionally be determined based on the angular sensitivity of the ultrasound detector UD in the RF transponder circuit RTC. For example, acoustic screening may be used to control the angular range over which ultrasound detector UD is sensitive to ultrasound signals. Moreover it is also contemplated to include a plurality of ultrasound detector elements in ultrasound detector UD in RF transponder circuit RTC and to include a phase adjustment unit configured to provide a predetermined phase delay for ultrasound signals detected by each detector element in the array, and a signal summation unit configured to provide a weighted sum of the phase-delayed ultrasound signals. In so doing the angular sensitivity of ultrasound detector UD in RF transponder circuit RTC may be controlled in order to determine the angular position of the RF transponder circuit RTC respective the ultrasound emitter unit UEU.

Returning to the RF transponder circuit RTC in FIG. 2; modulator MOD may include electrical circuits or a processor that exploits one of the following exemplary techniques: i) changing a frequency of the RF signals emitted or reflected by the RF transponder circuit RTC; ii) changing a phase of the RF signals emitted or reflected by the RF transponder circuit RTC; iii) changing an amplitude of the RF signals emitted or reflected by the RF transponder circuit RTC; iv) changing a pulse sequence of the RF signals emitted or reflected by the RF transponder circuit RTC; v) changing a code encoded in the RF signals emitted or reflected by the RF transponder circuit RTC. A combination of these techniques or indeed other modulation techniques may also be implemented by modulator MOD.

Preferably the parameter that is changed is continuously variable across a predetermined range in an analog fashion, although digital switching of the parameter between one of a plurality of discrete levels is also contemplated. Corresponding RF transponder circuit RTC in FIG. 1 may of course likewise exploit one or more of these modulation techniques.

The above modulation techniques may be exploited by various RF transponder circuit RTC circuits in order to modulate either their reflectance of RF signals, or to modulate their emitted RF signals. The reflectance of RF signals may for example be modulated using techniques commonly used in the RFID and NFC field such as load modulation, or reflected backscatter. The emitted RF signals may be modulated using other known circuits such as those from the NFC field. The reflectance and the emission modulation techniques may also use principles that are known from the RF communications field in general. Thus various electronic components may be used in RF transponder circuit RTC, including passive and active electronic components, and optionally one or more processors. In the present invention the RF transponder circuit RTC circuits further include circuitry that provides for the desired modulation in response to detected ultrasound signals.

Considering firstly the use of reflectance modulation in the RF transponder circuit. This may be used with each of the above RF modulation schemes. Here, the techniques of load modulation or backscatter radiation modulation that are known from the RFID field may be used. In load modulation, an RF emitter such as RF emitter RFE generates an RF field that is used to power the RF transponder circuit. Energy is transferred to the circuit by virtue of the bandwidth of frequencies emitted by the RF emitter overlapping with a resonant frequency of the RF transponder circuit. The RF transponder circuit subsequently uses this power to modulate its own impedance. This modulation in the impedance, or load, is "seen" by the RF emitter or the RF detector. The modulation of the load is made in accordance with a desired 1-bit or multi-bit code that is desired to be transmitted to the RF emitter or RF detector. In effect, the RF reflectance of the RF transponder circuit is modulated by modulating its impedance. A preferred electrical circuit that exploits reflectance modulation technique is shown in FIG. 3. FIG. 3 illustrates an RF transponder circuit RTC in which modulation is provided by a varactor diode VAR1 that forms part of a series LCR tuned circuit. The series LCR tuned circuit in FIG. 3 has a resonance frequency determined in accordance with the equation:

$$f_{resonant} = \frac{1}{2\pi \cdot \sqrt{L \cdot C}}$$ Equation 1

In FIG. 3, the capacitance of ultrasound detector UD and the inherent stray capacitance of the varactor diode VAR1 provide the capacitance C in Equation 1. Ultrasound detectors, particularly capacitive ultrasound detectors, magnetostrictive detectors, MEMS and CMUT detectors inherently have such a stray capacitance. Additional capacitors may be included in the circuit of FIG. 3 to adjust the resonant frequency. Varactor diode VAR1 performs the modulation, a varactor being an electronic component having a capacitance that varies with the bias voltage $V_D$ across it. The inductance L in Equation 1 is provided by the inductance of antenna AN in FIG. 3. In this particular circuit antenna AN serves both to receive RF signals from RF emitter RFE, and to reflect RF signals from RF transponder circuit RTC. The resistance in the series LCR tuned circuit is provided by the inherent stray resistance of the electrical conductors connecting the components although additional dedicated resistors may also be provided.

In operation the circuit of FIG. 3 receives RF signals via antenna AN by magnetic or capacitive coupling or a combination thereof from RF emitter RFE. These RF signals, particularly the magnetic component thereof when in the near-field, thus energize RF transponder circuit RTC. The tuned circuit has an electrical resonance frequency, e.g. $F_{ElRes1}$, governed by Equation 1 above, when the voltage $V_D$ across varactor diode VAR1 is at a first voltage $V_{D1}$. Voltage $V_D$ is controlled at least in part by the electrical signals generated by ultrasound detector UD. In order to provide efficient power transfer, preferably the RF signals emitted by RF emitter unit RFE have a bandwidth that overlaps with the electrical resonance frequency of the RF transponder circuit RTC, i.e. $F_{ElRes1}$. In a first operational mode in the absence of ultrasound signals from ultrasound emitter unit UEU, the tuned circuit, which is energized by RF signals from RF emitter RFE, resonates at an electrical resonance frequency $F_{ElRes1}$. This resonance is seen as an impedance by the RF emitter unit RFE and operates to reflect some of the emitted RF signals. These RF signals at $F_{ElRes1}$ may subsequently be detected by a detector such as RF detector unit RFD in FIG. 1. When ultrasound detector UD receives ultrasound signals from ultrasound emitter unit UEU, the electrical signals generated by ultrasound detector UD change the voltage $V_D$ across varactor diode VAR1 from the first voltage $V_{D1}$ to a second voltage $V_{D2}$. Consequently the tuned circuit has a second electrical resonance frequency $F_{ElRes2}$; this being determined in accordance with Equation 1. In this second operational mode the tuned circuit presents a different impedance to the RF signals emitted by RF emitter unit RFE, and thus a different reflectance to these signals. In other words the varactor diode in the RF transponder circuit RTC in FIG. 3 operates as a modulator that modulates the reflectance of the RF transponder circuit to RF signals. More specifically the varactor diode can be considered to modulate both the frequency and the amplitude of RF signals reflected by the RF transponder circuit.

It should be noted that whilst the symbol for an inductor is shown in FIG. 3 to represent the inductance in Equation 1, this inductor may be provided by antenna AN in the form of a short length or a loop of conductor having a low, or parasitic, inductance value. Particularly at high frequencies, the parasitic inductance of such a conductor is typically adequate to provide the desired energy transfer and resonance in accordance with Equation 1.

Moreover, FIG. 3 is only illustrative of one specific electrical circuit for providing reflectance modulation. Alternative circuits to that in FIG. 3 may also be used in which a resonant, or tuned circuit is de-tuned in order to provide the desired change in reflectance. These include parallel LCR resonant circuits in which an ultrasound detector converts received ultrasound signals into electrical signals that are used to change the voltage across a varactor diode and thereby change the circuit's resonance frequency. Moreover, such circuits may include additional electronic components such as FET switches and resistors as described later.

Figure 5B:
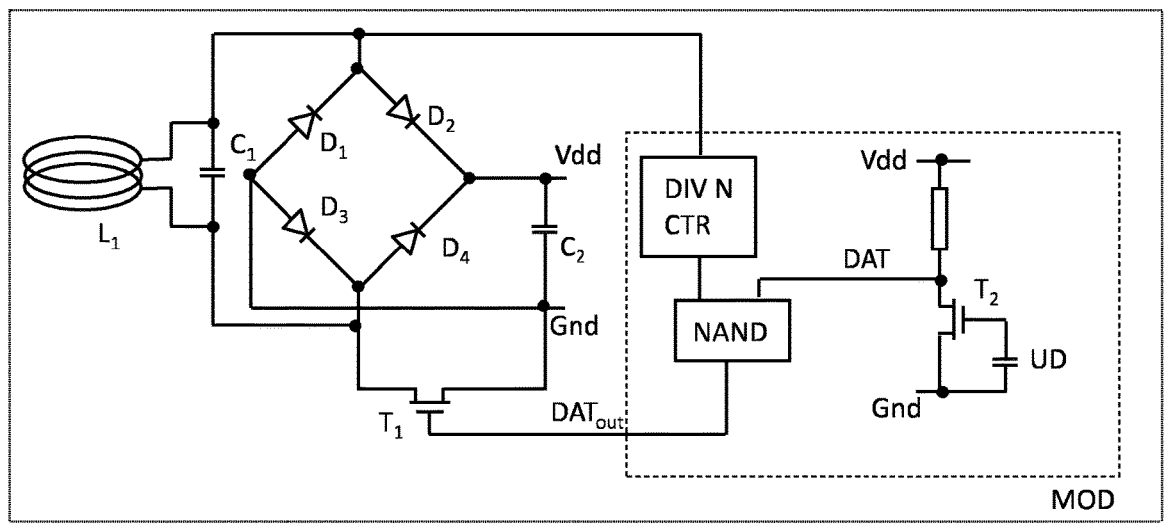

FIG. 5A illustrates another exemplary RF transponder circuit RTC together with an exemplary RF emitter RFE and an exemplary RF detector RFD. The circuit in FIG. 5A uses load modulation to change its reflectance to RF signals. In the circuit of FIG. 5A, oscillator Osc generates RF signals that are coupled to an emitter coil, i.e. an antenna, by means of resistor $R_0$ and capacitor $C_0$. Capacitor $C_0$ may be used to adjust a resonance frequency of the electrical circuit defined by capacitor $C_0$ and the inductance of the emitter coil. Oscillator Osc, resistor $R_0$, capacitor $C_0$ and the emitter coil together form RF emitter RFE. In operation the emitter coil radiates RF signals in the form of oscillating magnetic field H, some of which RF signals couple to a corresponding receiver coil, i.e. antenna, $L_1$, that forms part of RF transponder circuit RTC. RF transponder circuit RTC includes diode $D_1$ and capacitor $C_2$ which together rectify and smooth the detected RF signals to generate a smoothed power supply across terminals Vdd-Gnd. Capacitor $C_1$ may be used to adjust a resonance frequency of the electrical circuit defined by capacitor $C_1$ and the inductance of the coil $L_1$. Exemplary RF transponder circuit RTC is thus in the form of a parallel LCR resonator and may have a parallel LCR resonance frequency determined in-part by the values of $L_1$ and $C_1$. Terminals Vdd-Gnd supply power to modulator MOD, whose data output at terminal DAT controls FET switch $T_1$. The RF transponder circuit RTC of FIG. 5A uses the load modulation principle described above to modulate its reflectance to RF signals such that RF radiation from RF emitter RFE is scattered back to RF detector RFD by RF transponder circuit RTC. Moreover, data at terminal DAT that is output from modulator MOD switches FET switch $T_1$, which changing the load impedance seen by RF detector RFD in accordance with the data. In one implementation the data at terminal DAT may be a single bit of data that is output by modulator MOD in response to detected ultrasound signals that were emitted by ultrasound emitter unit UEU in FIG. 1. In this implementation, modulator MOD may for example include an ultrasound detector UD and a FET switch $T_2$ that are connected in series, as illustrated in FIG. 5B for generation of the desired 1-bit data at terminal DAT, i.e. a logic 1 or a logic 0. Alternative implementations of modulator MOD may include for example a memory and a shift register that are arranged to serially output a multi-bit data word, i.e. a code, from the memory to terminal DAT when so-triggered by a detected ultrasound pulse. Moreover, in addition to digital switching, the FET switch may be used in an analogue mode to provide an analogue change in reflectance in response to an input ultrasound signal. In another implementation the exemplary series arrangement of FET switch $T_2$ and the resistor in FIG. 5B may be used in the circuit of FIG. 5A to control a voltage controlled oscillator or a phase shifter in modulator MOD in order to effect 1-bit or multi-bit data transfer to RF detector RFD via phase shift modulation, or frequency modulation "frequency shift keying" respectively. It is to be note that throughout the electronic circuits disclosed herein, bipolar switches may, as appropriate, be used to replace the illustrated FET switches. When bipolar switches are used, it may clearly be more appropriate to connect these in series in a circuit rather than to shunt the coil $L_1$. Thus, the collector and emitter terminals of a bipolar switch in FIG. 5A might be connected in series between diode $D_1$ and coil $L_1$ with an ultrasound detector connected between its base and emitter as an alternative to FET transistor $T_1$.

In order to detect the RF signals reflected by RF transponder circuit RTC, RF detector circuit RFD in FIG. 5A may include a bandpass filter BPF, an amplifier AMP and a demodulator DEMOD. As outlined above, the switching of FET switch $T_1$ in FIG. 5A modulates the load impedance seen by RF detector RFD. This causes a corresponding modulation of the backscattered radiation, i.e. a modulation of the radiation reflected by RF transponder circuit RTC. The backscattered radiation is detected as a modulated RF signal by the RF emitter coil, or antenna, of RF emitter RFE. The modulated signal is filtered by bandpass filter BPF to reduce interference and noise, amplified by amplifier AMP, and subsequently demodulated by demodulator DEMOD to provide the original modulation signal that originated at terminal DAT, at terminal DAT'.

The time delay between the detection of the demodulated signal at terminal DAT', and the signal that caused ultrasound emitter unit UEU in FIG. 1 to emit the ultrasound pulse may subsequently be computed in a position determination unit PDU in order to determine the range between the ultrasound emitter unit UEU that emitted the ultrasound pulse and the RF transponder circuit RTC. The choice of demodulation circuit DEMOD in FIG. 5A corresponds to the modulation type that is used, and various circuits detailed in the above referenced handbooks may be selected used for this purpose. Moreover, although in the implementation of FIG. 5A the RF emitter circuit RFE and the RF detector circuit RFD share an antenna or coil, other implementations may also be used in which the RF emitter circuit RFE and the RF detector circuit RFD have separate antennae.

FIG. 5B illustrates another exemplary RF transponder circuit RTC which employs load modulation to modulate backscattered radiation. RF transponder circuit RTC in FIG. 5B may be used in place of the same-named item RTC in FIG. 5A to provide reflectance modulation. In operation, coil $L_1$ of RF transponder circuit RTC in FIG. 5B intercepts magnetic field lines H in FIG. 5A and converts these to an electric current. The electric current is rectified by full wave rectifier diodes $D_1$-$D_4$ and smoothed by capacitor $C_2$ to generate a smoothed power supply across terminals Vdd-Gnd. RF transponder circuit RTC in FIG. 5B may have a resonance frequency determined in-part by the values of $L_1$ and $C_1$. Terminals Vdd-Gnd supply power to modulator MOD. The data output terminal of modulator MOD, $DAT_{mod}$ controls FET switch $T_1$. In operation the circuit of FIG. 5B includes a divide-by-n counter, DIV N CTR which provides a signal at a frequency that is $1/n^{th}$ of the frequency of the RF signal detected by RF transponder circuit RTC. The logical NAND of this signal and the data at terminal DAT is then used to switch FET switch $T_1$ to, as in FIG. 5A, change the load impedance seen by RF detector RFD in FIG. 5A. In the illustrated implementation the data at terminal DAT is a single bit of data that is generated by modulator MOD in response to ultrasound signals that are detected by ultrasound detector UD. In this, a detected ultrasound pulse causes a high signal at the input to FET switch $T_2$. This then causes a low signal at terminal DAT. Multiple ultrasound pulses may trigger DAT several times in the same way. In so doing, a 1-bit data word at terminal DAT, i.e. a logic 1 or a logic 0 causes FET switch $T_1$ to modulate the backscattered RF signal detected by RF detector RFD in FIG. 5A and thereby signals to RF detector RFD that an ultrasound pulse has been detected by RF transponder circuit RTC. In the implementation of FIG. 5B the divide-by-n counter synchronizes the detected signal with the emitted signal which aids the demodulation process in RD detector RFD. Specifically, it provides two frequency-shifted sideband signals at a frequency separation determined by the detected frequency divided by n, wherein the amplitude of the sideband signals is controlled by the data value at terminal DAT. Thus, the circuit of FIG. 5B provides amplitude modulation of the frequency-shifted sideband signals. As described in relation to FIG. 5A, variations of the circuit in FIG. 5B may include for example a memory and a shift register in modulator MOD that serially outputs a multi-bit data word, i.e. a code, at terminal DAT when the ultrasound detector detects an ultrasound pulse. In another implementation the detection of an ultrasound signal by the exemplary series arrangement of FET switch $T_2$ and the resistor in FIG. 5B may instead be arranged to control a voltage controlled oscillator or a phase shifter in modulator MOD in order to provide 1-bit or multi-bit data transfer to RF detector RFD via phase shift modulation, or frequency modulation "frequency shift keying" respectively.

Figure 6:
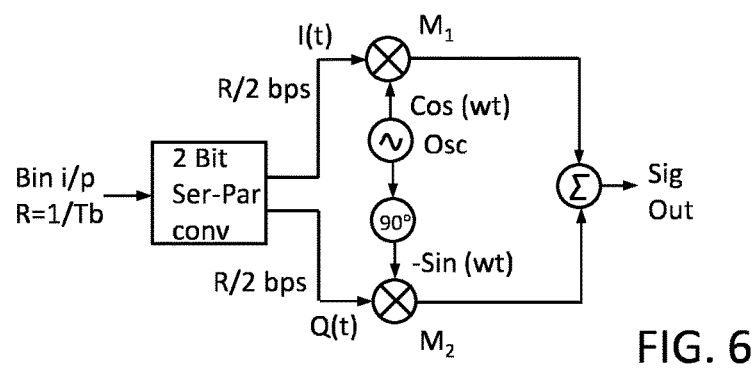
FIG. 6 illustrates an exemplary schematic diagram of a phase modulator circuit.

FIG. 6 illustrates an exemplary schematic diagram of a phase modulator circuit. The phase modulator circuit in FIG. 6 may be used to implement modulator MOD in FIG. 5A and FIG. 5B as an alternative to the modulators described above. FIG. 6 implements a so-called phase shift keying, PSK, technique in which the phase of an RF signal is modulated. The circuit of FIG. 6 may be connected with an ultrasound detector UD in order to perform phase modulation of an RF signal reflected by RF transponder circuit RTC. The exemplary circuit of FIG. 6 may be powered by the rectified signals delivered to power terminals Vdd and Gnd from either of the circuits of FIG. 5A and FIG. 5B. In FIG. 6 an RF oscillator Osc provides two mutually phase-shifted signals Cos(wt) and Sin(wt). Signal multipliers $M_1$, $M_2$ multiply the mutually-phase sifted signals by an in-phase signal I(t) and a quadrature signal Q(t) respectively. The multiplied signals are then summed at unit Sigma to provide an output signal at terminal Sig Out. Terminal Sig Out corresponds to data terminal DAT in FIG. 5A or FIG. 5B. The in-phase signal I(t) and the quadrature signal Q(t) are received from 2-bit serial-to-parallel converter 2 Bit Ser-Par cony. The 2-bit serial-to-parallel converter 2 Bit Ser-Par cony is input with a 1-bit or a multi-bit word at terminal Bin i/p, and splits consecutive input bits into outputs I(t) and Q(t) in order to generate the desired phase modulation at terminal Sig Out. In order to transmit a 1-bit word with the circuit of FIG. 6 the signals sent to outputs I(t) and Q(t) may for example be the same. In order to modulate the reflectance of an RF transponder circuit RTC, terminal Bin i/p of the FIG. 6 modulator may be connected to the output terminal DAT of the FET switch $T_2$ in FIG. 5B by means of a shift register and memory that stores a multi-bit word. In operation, the detection of an ultrasound pulse by ultrasound detector UD in FIG. 5B causes output terminal DAT of FET switch $T_2$ to trigger the serial shifting of the multi-bit word from the memory and into terminal Bin i/p of the modulator of FIG. 6 via the shift register. The subsequently phase-shift modulated signal at terminal Sig Out in FIG. 6 may subsequently trigger FET switch $T_1$ in the RF transponder circuit RTC in either FIG. 5A or FIG. 5B in order to modulate the signals reflected by the RF transponder circuit RTC. Subsequently the modulated signals, are detected by RF detector circuit RFD in FIG. 5A and the transmitted code is recovered at terminal DAT'. A single-bit code may be transmitted by this arrangement in the same way.

Thus, as described above, a variety of electrical circuits may be used by RF transponder circuit RTC to modulate the signals reflected by the RF transponder circuit RTC.

Similar amplitude modulation, frequency modulation, phase modulation, and encoding principles to those described above may also be used to modulate the signals emitted by an RF transponder circuit such as RF transponder circuit RTC in FIG. 1. In this context, various electrical circuits that are known for use in both RFID and NFC may be adapted using general electronic circuit design practice, to include an ultrasound detector in order to provide the desired modulation of RF signals emitted in response to detected ultrasound signals. These may include electrical circuits that continuously emit RF signals, the modulation of the emitted RF signals being changed in accordance with a detected ultrasound signal, and electrical circuits that emit RF signals with a predetermined modulation when triggered to do so by a detected ultrasound signal. Thereto, principles known from handbooks such as "RFID handbook—Fundamentals and Applications in contactless smart cards, radio frequency identification and near field communication, Third Edition, Klaus Finkenzeller, Giesecke & Devrient GmbH, Munich, Germany, WILEY, 2010, ISBN: 978-0-470-69506-7" and "The RF and Microwave handbook, 2001, Editor in Chief Mike Golio, CRC press, ISBN 13:978-1-4200-3676-3" may be adapted to include the desired frequency modulation, phase modulation, or encoding of the RF signals emitted by the RF transponder circuit RTC in response to detected ultrasound signals. In accordance with the present invention, these RF transponder circuits share the concept of using the RF emitter unit RFE as the power source to the RF transponder circuit RTC, as was described in relation to reflectance modulation, and that modulation is provided in response to ultrasound signals that are detected by an ultrasound detector UD. In contrast to the above-described reflectance modulation circuits, the RF transponder circuits that modulate emitted RF signals may generate sufficient current in its antenna AN for the resulting RF signal to be detected by a receiving antenna of an RF detector unit RFD.

Moreover, known electronic transceiver and transponder circuits that are used in the field of NFC, such as those disclosed in documents US2011/0043429A1 and US2010/0167644A1 may be adapted in a similar manner to the circuits described above to include an ultrasound detector UD in order to provide any of the desired frequency modulation, amplitude modulation, phase modulation, or encoding of the RF signals emitted by the RF transponder circuit RTC. In such NFC-type circuits, communication of data between NFC communicators may be via an "active" communication mode in which the NFC communicator, i.e. RF emitter RFE, transmits an alternating magnetic field that is modulated with data to be communicated and the receiving NFC communicator, i.e. RF transponder circuit RTC, responds by transmitting or generating its own modulated magnetic field, or via a "passive" communication mode in which one NFC communicator i.e. RF emitter RFE transmits an alternating magnetic field and maintains that field and the responding NFC communicator, i.e. RF transponder circuit RTC, modulates the magnetic field to which it is inductively coupled with the data to be communicated, for example by modulating the load on the inductive coupling, i.e. load modulation. A combination of load modulation, in order to modulate the reflected RF signals, and emitted RF signal modulation, may thus also be used by these circuits. Moreover any of the above circuit design principles may be combined as desired in order to provide the desired frequency modulation, phase modulation, or encoding of the RF signals reflected by or emitted by the RF transponder circuit RTC.

Returning to FIG. 1, the design of the corresponding RF detector unit RFD in FIG. 1 that detects the RF signals emitted or reflected by RF transponder circuit RTC clearly corresponds to the particular modulation technique employed by RF transponder circuit RTC. Position determination unit PDU subsequently monitors the time at which the ultrasound emitter unit UEU emitted a corresponding ultrasound signal and the time of any change in the modulation in order to determine the time difference $\Delta T_1$ and thus determine the position of RF transponder circuit RTC respective the ultrasound emitter unit UEU. Thus various known demodulation techniques from the field of RF communications may be included within RF detector unit RFD in order to detect the time of the modulation in the RF signal emitted or reflected by the RF transponder circuit RTC. When it is (i) a frequency of the RF signals emitted or reflected by the RF transponder circuit RTC that is modulated by the RF transponder circuit RTC, RF detector unit RFD may for example include a demodulator comprising a mixer that is configured to mix the detected RF signal with an RF signal having a frequency corresponding to an expected RF frequency of the RF detector unit RFD in the absence of an ultrasound signal. The result of the mixing includes a difference frequency that is at DC in the absence of an ultrasound signal. When an ultrasound signal is detected by the RF detector unit RFD the difference frequency will shift from DC. Thus the time of detection by the RF detector unit RFD of the corresponding modulation in the RF signal emitted or reflected by the RF transponder circuit RTC can be determined by monitoring the time of any changes in this difference frequency and thus used to determine the desired time difference $\Delta T_1$. Such a demodulator may be provided by electronic circuitry or by a processor.

Likewise when it is (ii) a phase of the RF signals emitted or reflected by the RF transponder circuit RTC that is modulated by the RF transponder circuit RTC, various known phase detection techniques including so-called phased locked loops, PLLs, or lock-in-amplifier circuits may be employed in the demodulator. In order to detect (iii) amplitude changes, the demodulator may employ a so-called phased locked loop, PLL, or a lock-in-amplifier. When it is (iv) a pulse sequence or (v) a code in the RF signals emitted or reflected by the RF transponder circuit RTC that is modulated by the RF transponder circuit RTC, the demodulator may include for example synchronous detection circuits for recovering amplitude, frequency or phase modulated signals, and optionally a shift register that is clocked by the detected pulse sequence to recover the original code. Again, in any of these techniques such demodulators may be provided by electronic circuitry or by a processor.

Thus in summary, and with reference to FIG. 1 a system SY for determining a position of an RF transponder circuit RTC respective an ultrasound emitter unit UEU based on RF signals emitted or reflected by the RF transponder circuit RTC is provided. The system includes an RF emitter unit RFE, an RF detector unit RFD, an ultrasound emitter unit UEU and a position determination unit PDU. The RF emitter unit RFE is configured to emit RF signals for energizing the RF transponder circuit RTC. The RF detector unit RFD is configured to detect RF signals emitted or reflected by the RF transponder circuit RTC. The ultrasound emitter unit UEU is configured to emit ultrasound signals for modulating the RF signals emitted or reflected by the RF transponder circuit RTC. Moreover, the position determination unit PDU is in operative communication with the RF detector unit RFD and with the ultrasound emitter unit UEU, and is configured to determine a position of the RF transponder circuit RTC respective the ultrasound emitter unit UEU based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC.

The RF transponder circuit RTC described above may, as mentioned, be attached to a wide variety of objects in order to facilitate their tracking via the determined position of the RF transponder circuit RTC.

Figure 7:
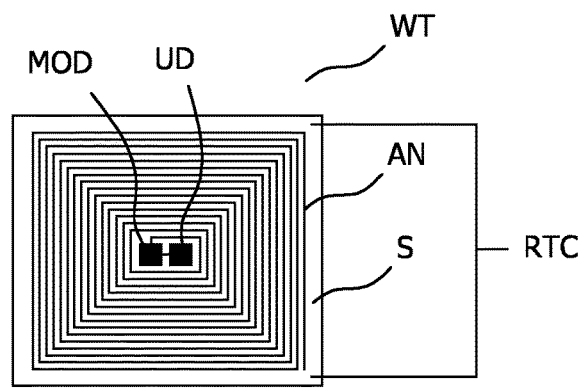
FIG. 7 illustrates a wireless tag WT comprising an RF transponder circuit RTC and a substrate S.

In one example implementation the RF transponder circuit RTC may be attached to a substrate for either tracking the substrate or tracking an object that the substrate is attached to. FIG. 7 illustrates a wireless tag WT comprising an RF transponder circuit RTC and a substrate S. The RF transponder circuit RTC is attached to the substrate S. RF transponder circuit RTC in FIG. 7 includes an antenna AN, modulator MOD and ultrasound detector UD. Moreover, as described above, when the RF transponder circuit RTC is attached to the substrate in this way, it is preferred that the frequency of the received ultrasound signals that cause a modulation of the RF signals emitted or reflected by the at least one antenna AN, i.e. the frequency of ultrasound signals emitted or reflected by the ultrasound emitter unit UEU, is different to the mechanical resonance frequency of the wireless tag or of the RF transponder circuit RTC, or of the substrate S. In so doing undesirable ultrasound-induced mechanical vibrations in these elements are avoided, thereby preventing that such ultrasound-induced mechanical vibrations interfere with the modulation of the RF signal that is detected by the RF detector unit RFD. By the term different it is meant that that the modulus of the difference between these frequencies expressed as a ratio of the mechanical resonance frequency preferably exceeds 10%, or 20% or 50% or 100%. Moreover, as described above, such unwanted mechanical vibrations may be avoided with the wireless tag by using ultrasound signals with frequencies that are greater than or equal to 40 kHz, or more.

Figure 8:
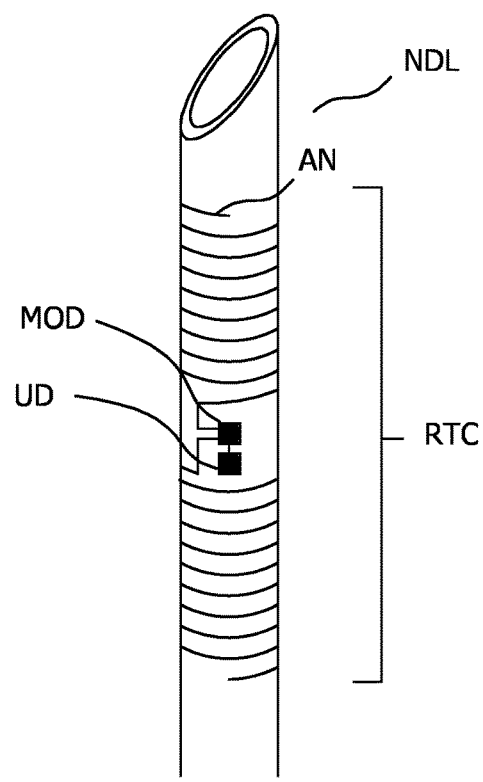
FIG. 8 illustrates a medical needle NDL that includes an RF transponder circuit RTC.

In another example implementation the RF transponder circuit RTC may be attached directly to the object that is to be tracked. FIG. 8 illustrates a medical needle NDL that includes an RF transponder circuit RTC. RF transponder circuit RTC in FIG. 8 includes an antenna AN in the form of a conductor that is wrapped around medical needle NDL in the form of a spiral, together with modulator MOD and ultrasound detector UD. Various adhesives, coating, or lamination techniques may be used to attach RF transponder circuit RTC to medical needle NDL. As described elsewhere, other types of antenna AN may be used in place of the spiral conductor.

Figure 9:
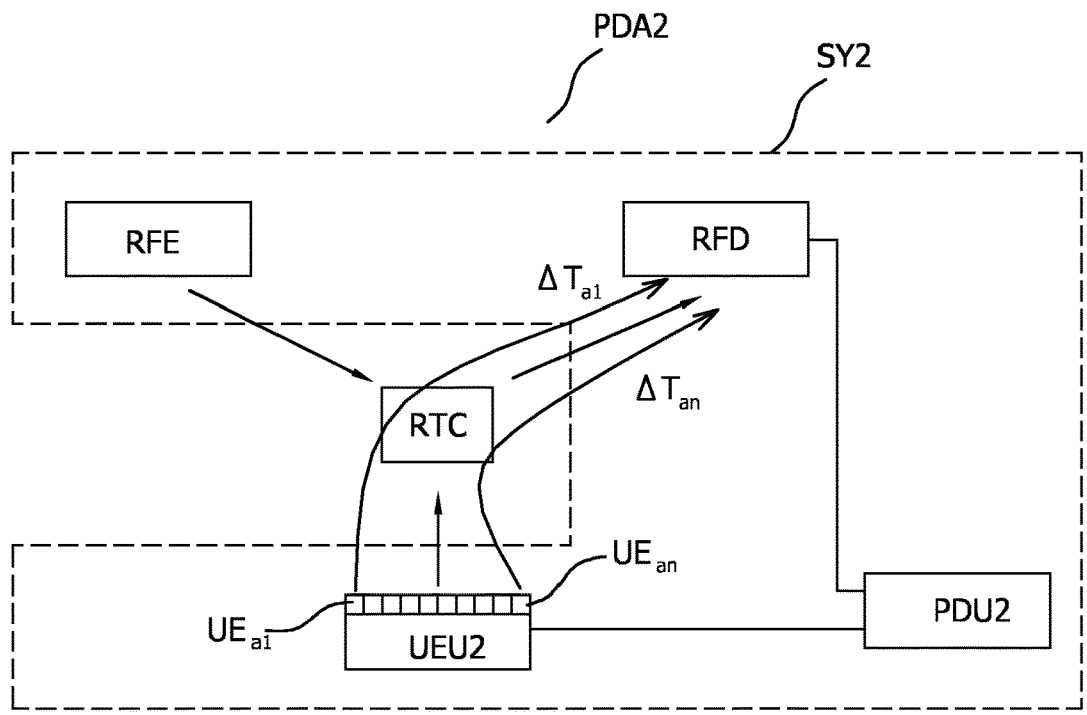
FIG. 9 illustrates a second embodiment of a position determination arrangement PDA2 that includes a system SY2 for determining a position of an RF transponder circuit RTC respective an ultrasound emitter unit UEU2, together with an RF transponder circuit RTC.

FIG. 9 illustrates a second embodiment of a position determination arrangement PDA2 that includes a system SY2 for determining a position of an RF transponder circuit RTC respective an ultrasound emitter unit UEU2, together with an RF transponder circuit RTC. The features in position determination arrangement PDA2 in FIG. 9 correspond to the features described above in relation to position determination arrangement PDA of FIG. 1. Furthermore, ultrasound emitter unit UEU2 in FIG. 9 includes a plurality of ultrasound emitters $UE_{a1 \ldots an}$; and position determination unit PDU2 is configured to determine a position of the RF transponder circuit RTC respective the ultrasound emitter unit UEU2 based on a set of time differences $\Delta T_{a1 \ldots an}$ between the emission of an ultrasound signal by each of the plurality of ultrasound emitters in the ultrasound emitter unit UEU2 and the detection by the RF detector unit RFD of its corresponding modulation in the RF signal emitted or reflected by the RF transponder circuit RTC.

In operation the position determination arrangement, PDA2, of FIG. 9 operates in much the same way as described in relation to FIG. 1. Additionally, the plurality of ultrasound emitters $UE_{a1 \ldots an}$ each emit an ultrasound signal that causes a corresponding modulation in the RF signal emitted or reflected by RF transponder circuit RTC, and thus in the signal detected by RF detector unit RFD. The ultrasound emitters thus generate a corresponding set of time delays $\Delta T_{a1 \ldots an}$ as illustrated in FIG. 9. Using triangulation, these time delays can be used to provide additional position information in relation to the position of RF transponder circuit RTC respective an ultrasound emitter unit UEU2. In one example configuration the time delays provided by two spatially-separated ultrasound emitters define an arc on which the RF transponder circuit RTC lies in relation to ultrasound emitter unit UEU2. In another example configuration, three ultrasound emitters in which one of the emitters is positioned away from an axis passing through the other two emitters may be used. Using triangulation, the three corresponding time delays provided by such an emitter arrangement may be used to identify a point in space on which the RF transponder circuit RTC lies in relation to ultrasound emitter unit UEU2. In other words, a plurality of emitters can be used to provide an angular position of RF transponder circuit RTC respective ultrasound emitter unit UEU2.

In order to improve discrimination between each of the ultrasound emitters in ultrasound emitter unit UEU2, each ultrasound emitter in UEU2 may for example be sequentially triggered to emit its ultrasound signal. Alternatively each ultrasound emitter in UEU2 may for example be caused to emit an ultrasound signal that has a different frequency or duration or pulse sequence to the ultrasound signals emitted by the other ultrasound emitters. Preferably all of the ultrasound emitters in ultrasound emitter unit UEU2 are synchronized to a common clock. The use of a common clock may improve recovery of the RF signals emitted or reflected by RF transponder circuit RTC; in part because each emitted ultrasound signal can be traced to a reference point in time.

The ultrasound emitter unit UEU2 described in relation to FIG. 9 may be provided by a plurality of individual ultrasound emitters that are arranged as described above. In a preferred configuration the ultrasound emitter unit UEU2 of FIG. 9 is provided by an ultrasound imaging probe that includes a plurality of ultrasound emitters $UE_{a1 \ldots an}$. Ultrasound imaging probes, such as a 2D imaging probe, a 3D imaging probe, a transesophageal TEE probe, transthoracic TTE probe, transnasal THE probe, intracardiac ICE probe conventionally include either a 1D linear array or a 2D array of ultrasound emitters. Thus, the ultrasound emitters of the ultrasound imaging probe may be used to generate the desired set of time differences $\Delta T_{a1 \ldots an}$ described above.

Ultrasound imaging probes typically employ beamforming techniques to generate a plurality of ultrasound beams in order to probe a region of interest. The use of such a beamforming ultrasound imaging probe as the ultrasound emitter unit UEU2 in FIG. 9, or indeed ultrasound emitter unit UEU in FIG. 1, offers other possibilities for determining the position of RF transponder circuit RTC respective the ultrasound emitter unit. These possibilities are now described with reference to a third embodiment illustrated in FIG. 10.

Figure 10:
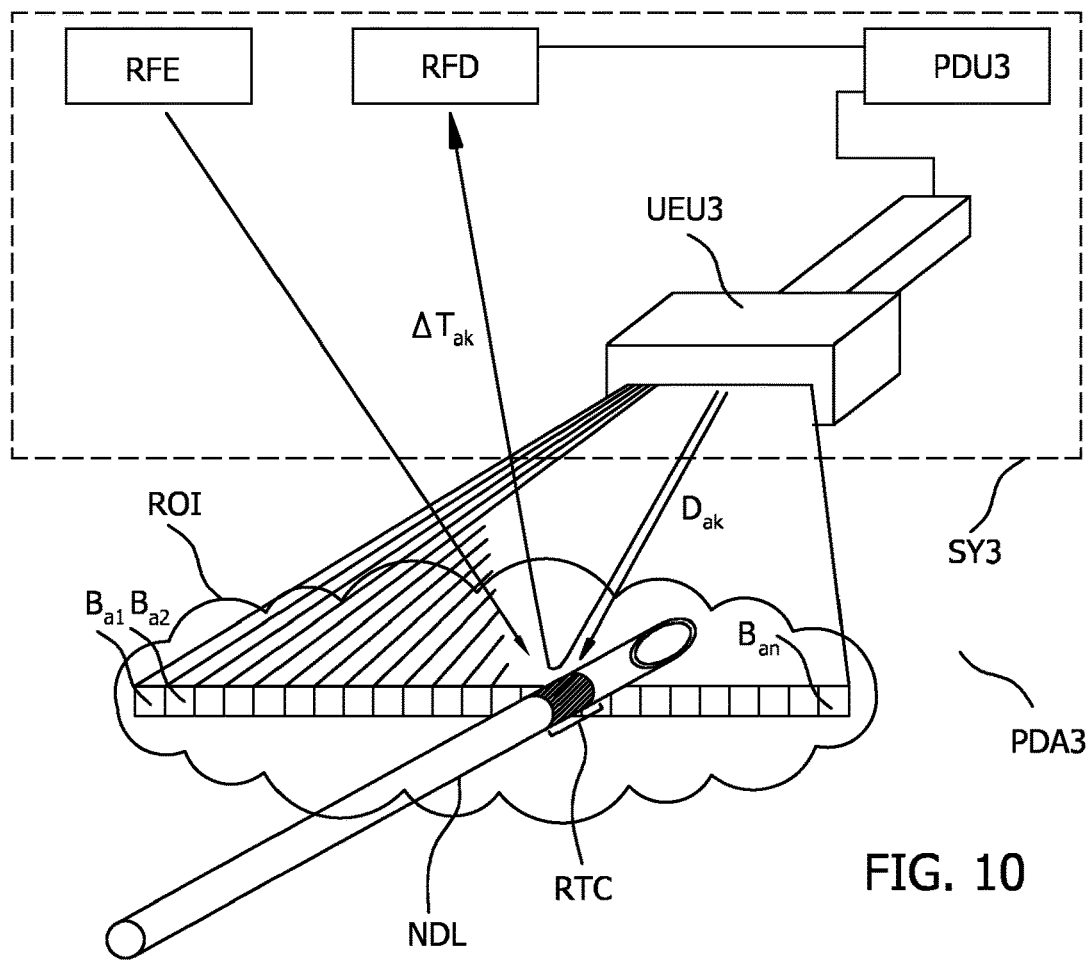
FIG. 10 illustrates a third embodiment of a position determination arrangement PDA3 that includes a system SY3 for determining a position of an RF transponder circuit RTC respective an ultrasound emitter unit UEU3, together with an RF transponder circuit RTC.

FIG. 10 illustrates a third embodiment of a position determination arrangement PDA3 that includes a system SY3 for determining a position of an RF transponder circuit RTC respective an ultrasound emitter unit UEU3, together with an RF transponder circuit RTC. RF transponder circuit RTC is attached to an exemplary medical needle NDL in FIG. 10 and may be used to track the position of the medical needle via the determined position of the RF transponder circuit RTC. Clearly other objects, including medical or interventional devices can be tracked in the same way as medical needle NDL. Ultrasound emitter unit UEU3 in FIG. 10 is provided by the ultrasound imaging probe of a beamforming ultrasound imaging system, and may for example be one of the imaging probe types described above. Such a beamforming ultrasound imaging system uses an array of ultrasound emitters $UE_{a1 \ldots an}$, not shown in FIG. 10, to generate plurality of ultrasound beams $B_{a1 \ldots an}$ in order to provide an ultrasound image corresponding to region of interest ROI.

Ultrasound emitter unit UEU3 in FIG. 10 corresponds to a conventional ultrasound imaging probe, and may include electronic driver and receiver circuitry, not shown, that is configured to amplify and/or to adjust the phase of signals transmitted by or received by ultrasound emitter unit UEU3 in order to generate and detect ultrasound signals in beams $B_{a1 \ldots an}$.

In operation, position determination unit PDU3 in FIG. 10 may be used to track the position of medical needle NDL via the position of RF transponder circuit RTC respective ultrasound emitter unit UEU3. This position may include the range or distance between the ultrasound emitter unit UEU3 and the RF transponder circuit RTC, and/or the angular position RF transponder circuit RTC respective the ultrasound emitter unit UEU3. The range, or distance $D_{ak}$ may be determined based on the time difference $\Delta T_{ak}$ between the emission of an ultrasound signal by the ultrasound emitter unit UEU3 corresponding to a particular beam, k, and the detection by the RF detector unit RFD of a corresponding modulation in the RF signal emitted or reflected by the RF transponder circuit RTC. In other words this is determined in a similar manner to that described in relation to FIG. 1 with the exception that this is performed for a particular ultrasound beam, k. The angular position RF transponder circuit RTC respective the ultrasound emitter unit UEU3 may be determined by identifying the particular ultrasound beam $B_{ak}$ in which RF transponder circuit RTC was located at the time of the corresponding modulation in the RF signal that was detected by the RF detector unit RFD.

More specifically, the angular position of RF transponder circuit RTC respective the ultrasound emitter unit UEU3 may be determined by correlating the ultrasound signals emitted by the ultrasound emitter unit UEU3 with the modulated RF signals detected by the RF detector unit RFD. In practical terms this correlation can include the steps of: constructing a matrix of possible positions for the RF transponder circuit within a plurality of ultrasound beams $B_{a1 \ldots an}$ of a beamforming ultrasound imaging probe UEU3 for each possible position, comparing a measured magnitude of modulation and/or a time difference $\Delta T_{ak}$ of an RF signal detected by the RF detector unit RFD with an expected magnitude of modulation and/or a time difference $\Delta T_{ak}$ of an RF signal detected by the RF detector unit RFD respectively; and identifying, based on the comparing step, a most likely position from the matrix of possible positions for the RF transponder circuit.

Other methods and algorithms for determining the position of the RF detector may also be used to carry out the above correlation.

Having thus determined the position of the RF transponder circuit RTC respective ultrasound emitter unit UEU3, the most likely position may be indicated in a corresponding ultrasound image of the region of interest ROI provided by the ultrasound emitter unit UEU3. Advantageously the position of the RF transponder circuit RTC is self-referenced to the ultrasound image because the position is determined in relation to the beams $B_{a1 \ldots an}$ of the beamforming ultrasound imaging system.

Figure 11:
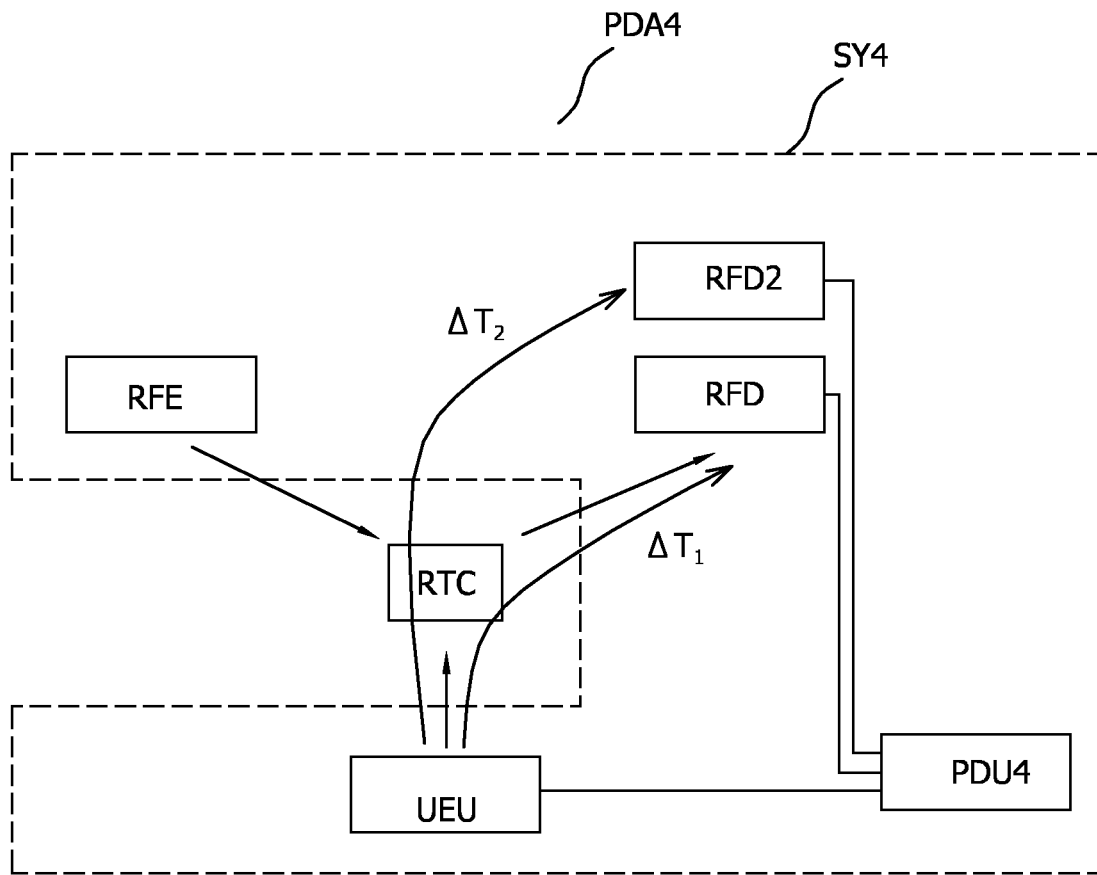
FIG. 11 illustrates a fourth embodiment of a position determination arrangement PDA4 that includes a system SY4 for determining a position of an RF transponder circuit RTC respective an ultrasound emitter unit UEU, together with an RF transponder circuit RTC.

FIG. 11 illustrates a fourth embodiment of a position determination arrangement PDA4 that includes a system SY4 for determining a position of an RF transponder circuit RTC respective an ultrasound emitter unit UEU, together with an RF transponder circuit RTC. In comparison to position determination arrangement PDA described in relation to FIG. 1, position determination arrangement, PDA4 additionally includes a second RF detector unit RFD2. RFD2 operates in the same way as RF detector unit RFD that was described in relation to FIG. 1 and is preferably positioned separately with respect to RF detector unit RFD. In comparison to position determination unit PDU described in relation to FIG. 1, position determination unit PDU4 is further configured to determine a position of the RF transponder circuit RTC respective the RF detector unit RFD and the at least a second RF detector unit RFD2. This position is based on a time delay $\Delta T_3$ between the time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC and a time difference $\Delta T_2$ between the emission of the ultrasound signal by the ultrasound emitter unit UEU and the detection by the at least a second RF detector unit RFD2 of the corresponding modulation in the RF signal emitted or reflected by the RF transponder circuit RTC. Otherwise the items in FIG. 11 operate in the same way as the corresponding items in FIG. 1.

Thus, in-use, the embodiment of FIG. 11 not only determines the position of RF transponder circuit RTC respective ultrasound emitter unit UEU, but also uses the time delay between $\Delta T_1$ and $\Delta T_2$ in FIG. 11 to provide the position of RF transponder circuit RTC respective the RF detector units RFD, and RFD2. Time delay $\Delta T_3$ is indicative of the difference in distance $D_3$ between RF transponder circuit RTC and the RF detector units RFD, RFD2. Distance $D_3$ may be determined by multiplying time delay $\Delta T_3$ by the speed of light since the RF detector units respond to the RF signals emitted or reflected by RF transponder circuit RTC. In so doing, improved positioning of the RF transponder circuit can be provided based on the predetermined positions of RF detector RFD and RF detector RFD2.

Figure 12:
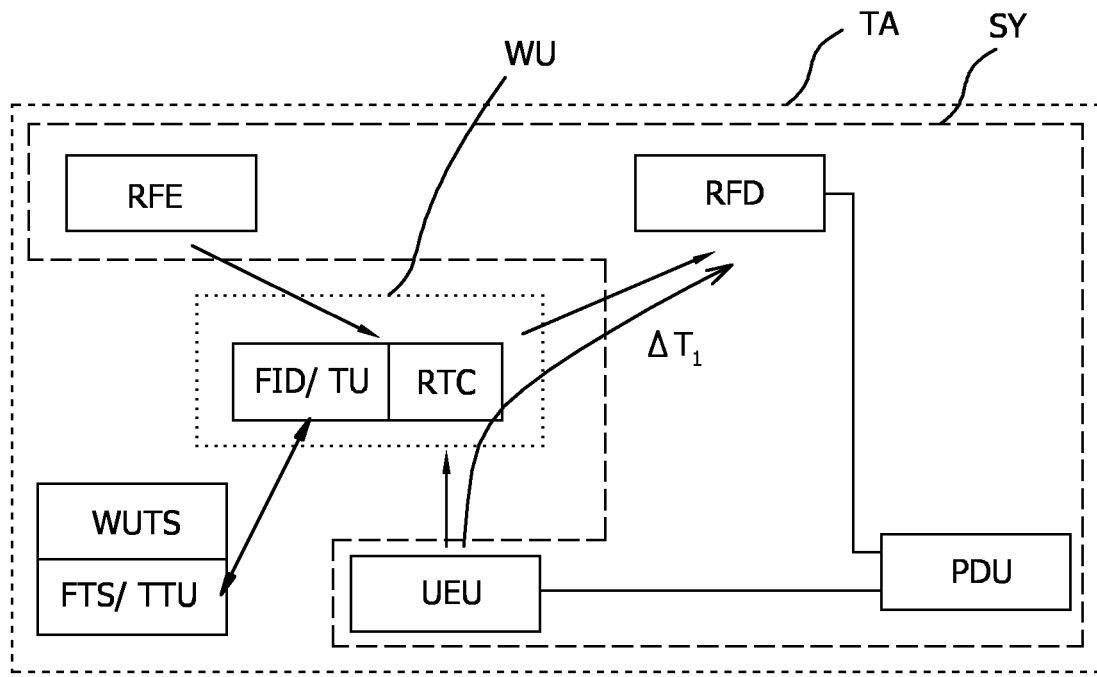
FIG. 12 illustrates a tracking arrangement TA that includes a system SY for determining a position of an RF transponder circuit RTC respective an ultrasound emitter unit UEU, a wireless unit tracking system WUTS and a wireless unit WU that includes an RF transponder circuit RTC and a fiducial FID or a transceiver unit TU.

FIG. 12 illustrates a tracking arrangement TA that includes a system SY for determining a position of an RF transponder circuit RTC respective an ultrasound emitter unit UEU, a wireless unit tracking system WUTS and a wireless unit WU that includes an RF transponder circuit RTC and a fiducial FID or a transceiver unit TU. System SY in FIG. 12 corresponds to the system described above with reference to FIG. 1 and operates in the same way to determine a position of RF transponder circuit RTC. As compared to FIG. 1, an additional fiducial FID or the transceiver unit TU is held in a fixed position with respect to the RF transponder circuit RTC, the two units defining a wireless unit WU. The two units are thus mechanically connected to one another. When a fiducial FID is used in wireless unit WU, the fiducial may be any device that is capable of being tracked by a magnetic tracking system or an optical or an ultrasound or an X-ray or a CT or a PET or a SPECT imaging system. Examples of such fiducials include a magnet or an electromagnet, optical retroreflectors, optical emitters such as visible or infrared LEDs; ultrasound fiducials configured to provide an ultrasound reflectance signature such as those made from gold, carbon, and polymers; "seeds" or coils that are detectable in an X-ray or CT image by means of their Hounsfield units absorption and which are typically formed from materials such as gold or carbon; and radioactive markers that can be detected in the nuclear image of a PET or SPECT imaging system. When a transceiver unit TU is used in wireless unit WU this may be any unit that is capable of receiving probe signals, and emitting in response thereto, return signals of one or more of ultrasound, electromagnetic, RF, microwave, infrared, and optical radiation. Such a transceiver unit is typically in the form of an electronic circuit. In one example, transceiver unit TU is an RF transceiver operating according to RFID or NFC communication principles. Thus, transceiver unit TU may include a passive RFID tag that performs load modulation in response to a received electromagnetic probe signal. A corresponding transceiver tracking unit TTU may include an electronic circuit that generates electromagnetic signals at a resonance frequency of the RFID tag, and that detects the range to the fiducial based on the signal intensity or on the time of flight as described above. Multiple such fiducial tracking system FTS generators and/or detectors may arranged in a spatially-separated configuration in order to triangulate the position of the fiducial. In another example transceiver unit TU includes an ultrasound detector that, upon reception of an ultrasound probe pulse of a predetermined frequency, emits an ultrasound or an optical or an RF return pulse to indicate its position. In another implementation transceiver unit TU may include an active electronic circuit that is sensitive to ultrasound signals, and which generates an ultrasound return signal in response thereto. The corresponding transceiver tracking unit TTU may include a signal generator that generates the probe signal, and a corresponding detector circuit that amplifies the detected return signal. The range between the transceiver tracking unit TTU and the transceiver unit TU can be determined based on the time of flight between the generated and detected signals, which is indicative of twice the range between the transceiver tracking unit TTU and the transceiver. The speed of propagation of ultrasound signals advantageously gives rise to a time delay that is measureable with low cost electronics. Several such detector and/or generator circuits may be arranged in a spatially-separated configuration in order to triangulate the position of the transceiver based on the respective times of flight.

Wireless unit tracking system WUTS in FIG. 12 includes a corresponding tracking system for tracking the position of fiducial FID or transceiver unit TU; i.e. a fiducial tracking system FTS or a transceiver tracking unit TTU. The fiducial tracking system FTS or a transceiver tracking unit TTU is configured to determine a position of the wireless unit WU, based on signals transmitted between i) the fiducial tracking system FTS and the fiducial FID, or between the ii) transceiver tracking unit TTU and the transceiver unit TU, correspondingly. When a fiducial tracking system FTS is used, this is either a magnetic tracking system or an optical or an ultrasound or an X-ray or a CT or a PET or a SPECT imaging system that is configured to provide an image that includes a position of the fiducial FID. For example, when an LED fiducial is used, the optical, or camera-based tracking system may be used to identify an angular position of the LED fiducial in the optical image. Multiple such cameras disposed about the LED fiducial may be used to determine a three-dimensional position of the fiducial via triangulation. A magnetic tracking system can be used to provide a magnetic image, i.e. a 2D or 3D map, that includes the position of the magnetic or electromagnet fiducial FID. When a transceiver tracking unit TTU is used, this may be used to determine an orientation and/or a range between the transceiver tracking unit TTU and the transceiver unit TU. This may for example be based on a time delay between emission of the triggering radiation and the detection of radiation received from the transceiver unit TU in response to the triggering radiation. Moreover the position may additionally or alternatively be based on intensity of the radiation received from the transceiver unit TU, or its position may be triangulated by using multiple, separated detectors for detecting the radiation received from the transceiver unit TU. Continuing the above example of a transceiver unit TU operating according to RFID or NFC communication principles; a position of the transceiver unit may be triangulated in three dimensions by using multiple RFID reader units.

In summary, wireless unit WU in FIG. 12 may therefore be tracked by means of two separate tracking systems: wireless unit tracking system WUTS and position determination unit PDU. This may be used to provide redundancy.

In one example implementation the tracking arrangement TA in FIG. 12 may be used to co-register two images. In this implementation ultrasound emitter unit UEU is an ultrasound imaging probe having an ultrasound field coordinate system UFCS. The ultrasound imaging probe may thus provide a first image. Ultrasound field coordinate system UFCS may for example be defined with respect to a point on ultrasound emitter unit UEU, and may for example be determined in polar or Cartesian or any other coordinate system. Moreover, fiducial tracking system FTS in FIG. 12 may be a magnetic tracking system or an optical or an ultrasound or an X-ray or a CT or a PET or a SPECT imaging system that is configured to provide a second image. The two images may be co-registered using the following method steps, which may be stored as instructions on a computer readable storage medium for execution on a processor controlling the tracking arrangement TA:

generating, with the ultrasound imaging probe, an ultrasound image in the ultrasound field coordinate system UFCS;

generating, with the fiducial tracking system FTS, a magnetic or an optical or an ultrasound or an X-ray or a CT or a PET or a SPECT image that includes a position of the fiducial FID;

causing the RF emitter unit RFE to emit RF signals for energizing the RF transponder circuit RTC;

causing the RF detector unit RFD to detect RF signals emitted or reflected by the RF transponder circuit RTC;

causing the ultrasound emitter unit UEU to emit ultrasound signals for modulating the RF signals emitted or reflected by the RF transponder circuit RTC; and determining a position of the RF transponder circuit RTC respective the ultrasound emitter unit UEU based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC; and mapping the ultrasound image to the image generated by the fiducial tracking system FTS by translating the ultrasound field coordinate system UFCS to a coordinate system of the fiducial tracking system FTS based on the determined position of the RF transponder circuit RTC respective the ultrasound emitter unit UEU and based on the position of the fiducial FID in the image generated by the fiducial tracking system FTS.

Figure 13:
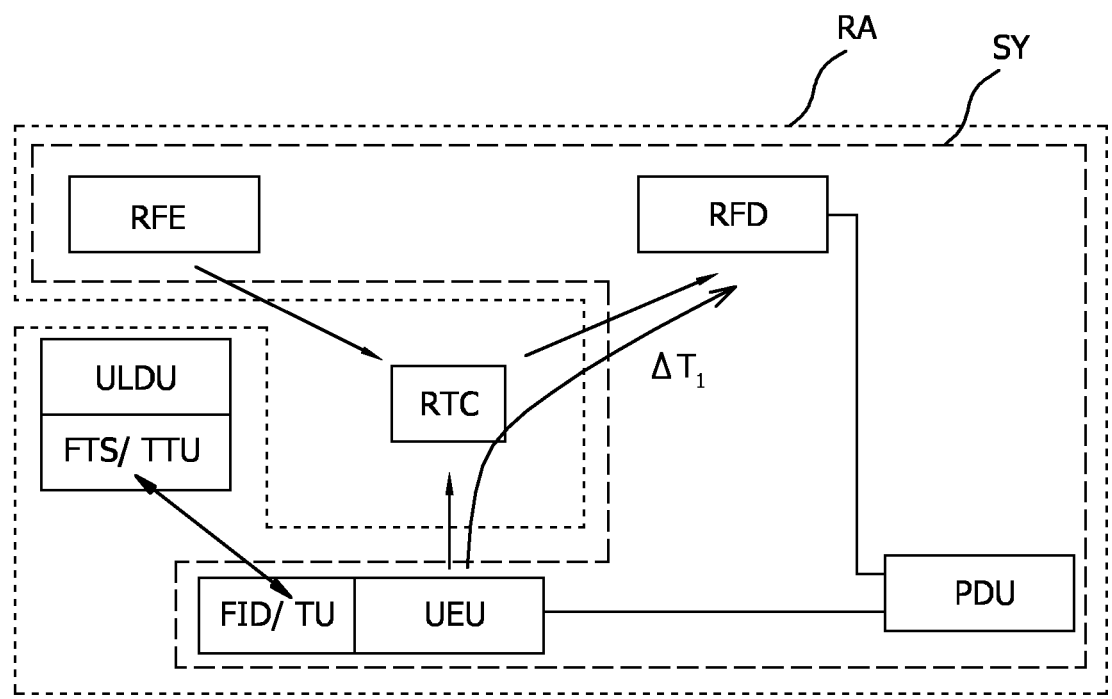
FIG. 13 illustrates a registration arrangement RA that includes a system SY in which ultrasound emitter unit UEU of system SY includes a fiducial FID or a transceiver unit TU, and an ultrasound emitter unit location determination unit ULDU that has a corresponding fiducial tracking system FTS or transceiver tracking unit TTU.

FIG. 13 illustrates a registration arrangement RA that includes a system SY in which ultrasound emitter unit UEU of system SY includes a fiducial FID or a transceiver unit TU, and an ultrasound emitter unit location determination unit ULDU that has a corresponding fiducial tracking system FTS or transceiver tracking unit TTU. System SY in FIG. 13 corresponds to the system described above with reference to FIG. 1 and operates in the same way to determine a position of RF transponder circuit RTC. As illustrated in FIG. 13, ultrasound emitter unit UEU of system SY additionally includes i) a fiducial FID or ii) a transceiver unit TU. The fiducial/transceiver unit is mechanically connected to ultrasound emitter unit UEU. When a fiducial FID is used, the fiducial may be any fiducial that is suitable for being tracked by an optical imaging system. Suitable fiducials are described above in relation to FIG. 12. Alternatively a transceiver unit TU as described in relation to FIG. 12 may be used. Registration arrangement RA in FIG. 13 also includes an ultrasound emitter unit location determination unit ULDU that has a corresponding i) fiducial tracking system FTS or ii) transceiver tracking unit TTU, configured to determine a position of ultrasound emitter unit UEU based on signals transmitted between the i) fiducial tracking system FTS and the fiducial FID, or between the ii) transceiver tracking unit TTU and the transceiver unit TU, correspondingly. Transceiver tracking unit TTU may be any of the corresponding units described in relation to FIG. 12. Fiducial tracking system FTS in FIG. 13 is an optical imaging system and is configured to provide an image that includes a position of the fiducial FID.

With reference to FIG. 13, in some implementations it may be useful to map the position of RF transponder circuit RTC as determined in a coordinate system of the ultrasound emitter unit UEU, to a coordinate system of the ultrasound emitter unit location determination unit ULDU. The latter coordinate system may serve as a global reference coordinate system. This is useful when for example the ultrasound emitter unit UEU is a mobile unit, such as for example an ultrasound imaging probe. Thereto, a computer-implemented mapping method is disclosed for use in a processor that controls the registration arrangement RA of FIG. 13. The method may for example be implemented by the same processor that implements the position determination method used by the above-described position determination unit PDU, or a separate processor. In one implementation, ultrasound emitter unit UEU in FIG. 13 may be an ultrasound imaging probe having an ultrasound field coordinate system UFCS as described in relation to FIG. 12. Registration arrangement RA in FIG. 13 may be used to map a position of RF transponder circuit RTC as determined in the coordinate system UFCS of the ultrasound emitter unit UEU, into a coordinate system ULDUCS of the ultrasound emitter unit location determination unit ULDU. The coordinate system ULDUCS, may be a polar or Cartesian or any other coordinate system and may have a different reference point to that of UFCS. The coordinate system ULDUCS may for example have a fixed reference point whereas the coordinate system UFCS may be mobile in space, particularly when defined in relation to a mobile ultrasound imaging probe. As described with reference to FIG. 9, when ultrasound emitter unit UEU2 in FIG. 9 is an ultrasound imaging probe, UEU2 can be used to accurately determine a position of the RF transponder circuit RTC respective the ultrasound emitter unit UEU2 based on a set of time differences $\Delta T_{a1 \ldots an}$ between the emission of an ultrasound signal by each of the plurality of ultrasound emitters $UE_{a1 \ldots an}$ in the ultrasound emitter unit UEU2 and the detection by the RF detector unit RFD of its corresponding modulation in the RF signal emitted or reflected by the RF transponder circuit RTC. The computer-implemented mapping method may include the steps of:

transmitting, from the transceiver tracking unit TTU of the ultrasound emitter unit location determination unit ULDU, probe signals for generating a return signal from the transceiver unit TU;

detecting, with the transceiver tracking unit TTU, return signals generated in response to the transmitted probe signals;

computing, based on the probe signals and the return signals, a position of the ultrasound emitter unit UEU, UEU2, UEU3 respective the ultrasound emitter unit location determination unit ULDU in a coordinate system of the ultrasound emitter unit location determination unit ULDUCS;

mapping a position of the RF transponder circuit RTC respective the ultrasound emitter unit UEU as determined by the position determination unit PDU of the system SY in the ultrasound field coordinate system UFCS, to the coordinate system of the ultrasound emitter unit location determination unit ULDUCS based on the position of the ultrasound emitter unit UEU respective the ultrasound emitter unit location determination unit ULDU.

In summary, a system for determining a position of an RF transponder circuit RTC respective an ultrasound emitter unit UEU has been described in which ultrasound signals emitted by the ultrasound emitter unit UEU modulate RF signals emitted or reflected by the RF transponder circuit RTC. The position of the RF transponder circuit RTC respective the ultrasound emitter unit UEU is subsequently determined based on a time difference $\Delta T_1$ between the emission of an ultrasound signal by the ultrasound emitter unit UEU and the detection by the RF detector unit RFD of a corresponding modulation in the RF signal emitted or reflected by the RF transponder circuit RTC.

Whilst the invention has been illustrated and described in detail in the drawings and foregoing description in relation to various medical devices, such illustrations and description are to be considered illustrative or exemplary and not restrictive; the invention is not limited to the disclosed embodiments and can be used for determining the position of objects in general. Moreover it is to be understood that the various examples and embodiments illustrated herein may be combined in order to provide various devices and methods for determining a position of an RF transponder circuit RTC respective an ultrasound emitter unit UEU.

The invention claimed is:

1. A system for determining a position of an RF transponder circuit, the system comprising:
an RF emitter configured to emit a first plurality of RF signals for energizing the RF transponder circuit;
an ultrasound emitter configured to emit a plurality of ultrasound signals;

the RF transponder circuit configured to reflect the first plurality of RF signals or emit a second plurality of RF signals, the RF transponder circuit comprising circuitry configured to, based on the plurality of ultrasound signals, electrically generate a modulation of the second plurality of RF signals emitted or a modulation of the first plurality of RF signals reflected by the RF transponder circuit, wherein the modulation includes at least one of: phase modulation, amplitude modulation, pulse sequence modulation, and code modulation;

an RF detector configured to detect the modulation of the second plurality of RF signals emitted or the modulation of the first plurality of RF signals reflected by the RF transponder circuit; and a position determination processor in operative communication with the RF detector and the ultrasound emitter, the position determination processor configured to determine the position of the RF transponder circuit respective to the ultrasound emitter based on a time difference between emission of an ultrasound signal of the plurality of ultrasound signals by the ultrasound emitter and detection by the RF detector of a corresponding modulation in a RF signal of the second plurality of RF signals emitted or a corresponding modulation of a RF signal of the first plurality of RF signals reflected by the RF transponder circuit.

2. The system according to claim 1, wherein the ultrasound emitter is configured to emit the plurality of ultrasound signals at a frequency that is greater than or equal to 40 kHz.

3. The system according to claim 1, wherein:
the RF emitter comprises an RF emitter antenna for transmitting the first plurality of RF signals to the RF transponder circuit; and
the RF emitter antenna is coupled to both the RF emitter and the RF detector such that the RF emitter antenna is configured to serve as an input to the RF detector for detecting the second plurality of RF signals emitted or the first plurality of RF signals reflected by the RF transponder circuit.

4. The system according to claim 1, wherein the RF transponder circuit has a mechanical resonance frequency and the ultrasound emitter is configured to emit the plurality of ultrasound signals at a frequency that is different from the mechanical resonance frequency of the RF transponder circuit.

5. The system according to claim 1, further comprising a plurality of ultrasound emitters that includes the ultrasound emitter; and
wherein the position determination processor is configured to determine the position of the RF transponder circuit based on a set of time differences between emission of an ultrasound signal by each of the plurality of ultrasound emitters and the detection by the RF detector of the corresponding modulation in the RF signal of the second plurality of RF signals emitted or the corresponding modulation of the RF signal of the first plurality of RF signals reflected by the RF transponder circuit.

6. The system according to claim 1, further comprising a second RF detector; and wherein:
the position determination processor is in operative communication with the second RF detector and further configured to determine the position of the RF transponder circuit respective the RF detector and the second RF detector based on a time delay between the time difference between emission of the ultrasound signal of the plurality of ultrasound signals by the ultrasound emitter and detection by the RF detector of the corresponding modulation in the RF signal of the second plurality of RF signals emitted or the RF signal of the first plurality of RF signals reflected by the RF transponder circuit and a time difference between emission of the ultrasound signal of the plurality of ultrasound signals by the ultrasound emitter and detection by the second RF detector of the corresponding modulation in the RF signal of the second plurality of RF signals emitted or the RF signal of the first plurality of RF signals reflected by the RF transponder circuit.

7. The system according to claim 1, wherein the RF detector is configured to wirelessly detect the second plurality of RF signals emitted or the first plurality of RF signals reflected by the RF transponder circuit.

8. The system according to claim 1, further comprising the RF transponder circuit, the RF transponder circuit (RTC) comprising:
at least one antenna configured to convert the first plurality of RF signals into first electrical signals for energizing the RF transponder circuit,
wherein an ultrasound detector configured to convert received ultrasound signals into second electrical signals;
and a modulator configured to receive the second electrical signals and to cause the at least one antenna to emit the second plurality of RF signals or reflect the first plurality of RF signals that are modulated based on the second electrical signals;
wherein the modulation includes at least one of:
i) changing a phase of the second plurality of RF signals emitted or the first plurality of RF signals reflected by the RF transponder circuit;
ii) changing an amplitude of the second plurality of RF signals emitted or the first plurality of RF signals reflected by the RF transponder circuit;
iii) changing a pulse sequence of the second plurality of RF signals emitted or the first plurality of RF signals reflected by the RF transponder circuit; and/or
iv) changing a code encoded in the RF signals the second plurality of RF signals emitted or the first plurality of RF signals reflected by the RF transponder circuit.

9. The system according to claim 8, wherein:
the modulator includes a varactor diode;
the varactor diode is connected to the antenna and to the ultrasound detector to provide a tuned circuit having a first electrical resonance frequency when the voltage across the varactor diode is at a first voltage; and
the ultrasound detector is connected to the tuned circuit such that when the ultrasound detector receives ultrasound signals, the second electrical signals generated by the ultrasound detector change the voltage across the varactor diode from the first voltage to a second voltage and the tuned circuit has a second electrical resonance frequency.

10. The system according to claim 8, wherein the modulator includes at least one of:
a frequency modulator configured to cause the at least one antenna to emit the second plurality of RF signals or reflect the first plurality of RF signals that are modulated based on the second electrical signals;
a phase modulator configured to cause the at least one antenna to emit the second plurality of RF signals or reflect the first plurality of RF signals that are modulated based on the second electrical signals;

an amplitude modulator configured to cause the at least one antenna to emit the second plurality of RF signals or reflect the first plurality of RF signals that are modulated based on the second electrical signals; and/or a pulse sequence encoder configured to cause the at least one antenna to emit the second plurality of RF signals or reflect the first plurality of RF signals that are modulated with a predetermined pulse sequence based on the second electrical signals.

11. The system according claim 8, wherein the RF transponder circuit is included in a wireless processor and the system further comprising i) a fiducial for being tracked by a magnetic tracking system, an optical, an ultrasound, an X-ray, a CT, a PET, or a SPECT imaging system, or ii) a transceiver responsive to at least one of ultrasound, electromagnetic, RF, microwave, infrared, and/or optical radiation; wherein the fiducial or the transceiver is held in a fixed position with respect to the RF transponder circuit.

12. The system according to claim 8, wherein the RF transponder circuit is a medical device selected from the group consisting of a needle, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, and a surgical tool.

13. The system according to claim 1, further comprising:
a wireless tracking system comprising either i) a fiducial tracking system or ii) a tracking transceiver, configured to determine a position of a wireless processor based on signals transmitted between i) the fiducial tracking system and a fiducial, or between ii) the tracking transceiver and a transceiver, correspondingly; and
wherein the fiducial tracking system is either a magnetic tracking system, an optical, an ultrasound, an X-ray, a CT, a PET, or a SPECT imaging system; and the fiducial tracking system is configured to provide an image that includes a position of the fiducial.

14. The system according to claim 13, wherein the ultrasound emitter is an ultrasound imaging probe having an ultrasound field coordinate system.

15. The system according to claim 14, further comprising a tracking processor configured to:
generate, with the ultrasound imaging probe, an ultrasound image in the ultrasound field coordinate system;
generate, with the fiducial tracking system, a magnetic or an optical or an ultrasound or an X-ray or a CT or a PET or a SPECT image that includes the position of the fiducial; cause the RF emitter to emit the first plurality RF signals for energizing the RF transponder circuit;
cause the RF detector to detect the second plurality of RF signals emitted or the first plurality of RF signals reflected by the RF transponder circuit;
cause the ultrasound emitter to emit ultrasound signals for modulating the second plurality of RF signals emitted or the first plurality of RF signals reflected by the RF transponder circuit; and
determine the position of the RF transponder circuit respective the ultrasound emitter based on the time difference between the emission of the ultrasound signal by the ultrasound emitter and the detection by the RF detector of the corresponding modulation in the RF signal of the second plurality of RF signals emitted or the corresponding modulation of the RF signal of the first plurality of RF signals reflected by the RF transponder circuit; and map the ultrasound image to the image generated by the fiducial tracking system by translating the ultrasound field coordinate system to a coordinate system of the fiducial tracking system based on the determined position of the RF transponder circuit respective the ultrasound emitter and based on the position of the fiducial in the image generated by the fiducial tracking system.

16. The system according to claim 1, further comprising a registration arrangement and wherein the ultrasound emitter further comprises i) a fiducial for being tracked by an optical imaging system, or ii) a transceiver responsive to at least one of ultrasound, electromagnetic, RF, microwave, infrared, and optical radiation; and wherein the fiducial or the transceiver is held in a fixed position with respect to the ultrasound emitter; the registration arrangement further comprises:
an ultrasound emitter processor comprising either i) a fiducial tracking system or ii) a tracking transceiver, configured to determine a position of the ultrasound emitter based on signals transmitted between i) the fiducial tracking system and the fiducial, or ii) the tracking transceiver and the transceiver, correspondingly; and
wherein the fiducial tracking system is an optical imaging system and is configured to provide an image that includes a position of the fiducial.

17. The system according to claim 16, wherein the ultrasound emitter is an ultrasound imaging probe having an ultrasound field coordinate system.

18. The system according to claim 17, wherein the registration arrangement includes the RF transponder circuit.

19. The system according to claim 18, further comprising a registration processor configured to:
transmit, from the tracking transceiver of the ultrasound emitter processor, probe signals for generating a return signal from the transceiver;
detect, with the tracking transceiver, return signals generated in response to the transmitted probe signals;
computing, based on the probe signals and the return signals, the position of the ultrasound emitter respective the ultrasound emitter processor in a coordinate system of the ultrasound emitter processor;
map the position of the RF transponder circuit respective the ultrasound emitter unit as determined by the position determination processor of the system in the ultrasound field coordinate system, to the coordinate system of the ultrasound emitter processor based on the position of the ultrasound emitter respective the ultrasound emitter processor.

20. The system according to claim 1, wherein, to detect the modulation of the plurality of RF signals, the RF detector comprises detector circuitry configured to demodulate the second plurality of RF signals emitted or the first plurality of RF signals reflected by the RF transponder circuit.

21. The system according to claim 1, wherein:
the RF emitter is further configured to generate and emit synchronization signals configured to demodulate the second plurality of RF signals emitted or the first plurality of RF signals reflected by the RF transponder circuit; and
the RF detector comprises detector circuitry configured to receive the synchronization signals and demodulate the second plurality of RF signals emitted or the first plurality of RF signals reflected by the RF transponder circuit based on the synchronization signals.

22. A non-transitory computer-readable storage medium having stored a computer program comprising instructions, which, when executed by a processor, cause the processor to:
- cause an RF emitter to emit a first plurality of RF signals for energizing an RF transponder circuit;
- cause an ultrasound emitter to emit a plurality of ultrasound signals;
- cause the RF transponder circuit configured to reflect the first plurality of RF signals or emit a second plurality of RF signals, the RF transponder circuit comprising circuitry configured to, based on the plurality of ultrasound signals, electrically generate a modulation of the second plurality of RF signals emitted or a modulation of the first plurality of RF signals reflected by the RF transponder circuit, wherein the modulation includes at least one of: phase modulation, amplitude modulation, pulse sequence modulation, and code modulation;
- cause an RF detector to detect modulation of the second plurality of RF signals emitted or the modulation of the first plurality of RF signals reflected by the RF transponder circuit; and
- determine a position of the RF transponder circuit respective the ultrasound emitter based on a time difference between emission of an ultrasound signal of the plurality of ultrasound signals by the ultrasound emitter and detection by the RF detector of a corresponding modulation in a RF signal of the second plurality of RF signals emitted or a corresponding modulation of a RF signal of the first plurality of RF signals reflected by the RF transponder circuit.

23. A computer-implemented method for determining a position of an RF transponder circuit, the method comprising:
- causing an RF emitter to emit a first plurality of RF signals for energizing the RF transponder circuit;
- causing an ultrasound emitter to emit a plurality of ultrasound signals;
- causing the RF transponder circuit configured to reflect the first plurality of RF signals or emit a second plurality of RF signals, the RF transponder circuit comprising circuitry configured to, based on the plurality of ultrasound signals, electrically generate a modulation of the second plurality of RF signals emitted or a modulation of the first plurality of RF signals reflected by the RF transponder circuit, wherein the modulation includes at least one of: phase modulation, amplitude modulation, pulse sequence modulation, and code modulation;
- causing an RF detector to detect the modulation of the second plurality of RF signals emitted or the modulation of the first plurality of RF signals reflected by the RF transponder circuit; and
- determining the position of the RF transponder circuit respective the ultrasound emitter based on a time difference between emission of an ultrasound signal of the plurality of ultrasound signals by the ultrasound emitter and detection by the RF detector of a corresponding modulation in a RF signal of the second plurality of RF signals emitted or a corresponding modulation of a RF signal of the first plurality of RF signals reflected by the RF transponder circuit.

\* \* \* \* \*